(12) United States Patent
Thenuwara et al.

(10) Patent No.: US 8,774,944 B2
(45) Date of Patent: *Jul. 8, 2014

(54) TOOLS, SYSTEMS, AND METHODS FOR INSERTING AN ELECTRODE ARRAY PORTION OF A LEAD INTO A BODILY ORIFICE

(75) Inventors: Chuladatta Thenuwara, Castaic, CA (US); Rosa Gallegos, Sylmar, CA (US); Timothy Beerling, Los Angeles, CA (US)

(73) Assignee: Advanced Bionics AG, Zug (CH)

( * ) Notice: Subject to any disclaimer, the term of this patent is extended or adjusted under 35 U.S.C. 154(b) by 771 days.

This patent is subject to a terminal disclaimer.

(21) Appl. No.: 12/824,122

(22) Filed: Jun. 25, 2010

(65) Prior Publication Data

US 2011/0319974 A1    Dec. 29, 2011

(51) Int. Cl.
*A61N 1/00*        (2006.01)
*A61B 17/34*       (2006.01)

(52) U.S. Cl.
CPC .................................. *A61B 17/3468* (2013.01)
USPC .......................................................... 607/137

(58) Field of Classification Search
CPC . A61N 1/0541; A61N 1/36032; H04R 25/00; A61B 17/3468
USPC .................... 607/136–137, 57, 116
See application file for complete search history.

(56) References Cited

U.S. PATENT DOCUMENTS

| | | | |
|---|---|---|---|
| 3,530,860 A | 9/1970 | Majoros | |
| 3,973,560 A | 8/1976 | Emmett | |
| 4,180,080 A | 12/1979 | Murphy | |
| 4,280,510 A | 7/1981 | O'Neill | |
| 4,488,561 A | 12/1984 | Doring | |
| 4,532,930 A | 8/1985 | Crosby et al. | |
| 4,646,755 A | 3/1987 | Kane | |

(Continued)

FOREIGN PATENT DOCUMENTS

| | | |
|---|---|---|
| EP | 0109304 | 5/1984 |
| EP | 0328597 | 8/1989 |

(Continued)

OTHER PUBLICATIONS

Non-Final Office Action received in U.S. Appl. No. 12/824,120, dated Jun. 8, 2012.

(Continued)

*Primary Examiner* — Christopher D Koharski
*Assistant Examiner* — Roland Dinga
(74) *Attorney, Agent, or Firm* — ALG Intellectual Property, LLC

(57) ABSTRACT

Exemplary insertion tools, systems, and methods for inserting an electrode array portion of a lead into a bodily orifice are described herein. An exemplary insertion tool includes a handle assembly, a retractor assembly disposed at least partially within the handle assembly, and a slider assembly disposed at least partially within the handle assembly. The retractor assembly may include a stiffening member configured to be inserted into an electrode array portion and a spring-loaded retractor member coupled to the stiffening member and configured to move from a distal position to a proximal position to at least partially retract the stiffening member from the electrode array portion. The slider assembly may be configured to selectively retain the spring-loaded retractor member and further configured to release the spring-loaded retractor member to move from the distal position to the proximal position in response to actuation by a user of the slider assembly.

14 Claims, 22 Drawing Sheets

(56) References Cited

U.S. PATENT DOCUMENTS

| | | | |
|---|---|---|---|
| 4,665,918 A | 5/1987 | Garza et al. | |
| 4,787,884 A | 11/1988 | Goldberg | |
| 4,819,647 A | 4/1989 | Byers et al. | |
| 4,865,037 A | 9/1989 | Chin et al. | |
| 4,898,183 A | 2/1990 | Kuzma | |
| 4,994,069 A | 2/1991 | Ritchart et al. | |
| 5,046,497 A | 9/1991 | Millar | |
| 5,110,529 A | 5/1992 | Arima | |
| 5,159,861 A | 11/1992 | Anderson | |
| 5,312,415 A | 5/1994 | Palermo | |
| 5,314,464 A | 5/1994 | KenKnight et al. | |
| 5,443,493 A * | 8/1995 | Byers et al. | 607/137 |
| 5,545,200 A | 8/1996 | West et al. | |
| 5,545,219 A | 8/1996 | Kuzma | |
| 5,558,673 A | 9/1996 | Edwards et al. | |
| 5,645,585 A | 7/1997 | Kuzma | |
| 5,667,514 A | 9/1997 | Heller | |
| 5,810,852 A | 9/1998 | Greenberg et al. | |
| 5,814,062 A | 9/1998 | Sepetka et al. | |
| 5,902,331 A | 5/1999 | Bonner et al. | |
| 5,906,619 A | 5/1999 | Olson et al. | |
| 5,999,859 A | 12/1999 | Jolly | |
| 6,070,105 A | 5/2000 | Kuzma | |
| 6,071,282 A | 6/2000 | Fleischman | |
| 6,078,841 A | 6/2000 | Kuzma | |
| 6,093,197 A | 7/2000 | Bakula et al. | |
| 6,119,044 A | 9/2000 | Kuzma | |
| 6,125,302 A | 9/2000 | Kuzma | |
| 6,129,753 A | 10/2000 | Kuzma | |
| 6,149,657 A | 11/2000 | Kuzma | |
| 6,163,729 A | 12/2000 | Kuzma | |
| 6,195,586 B1 | 2/2001 | Kuzma | |
| 6,208,882 B1 | 3/2001 | Lenarz et al. | |
| 6,219,580 B1 | 4/2001 | Faltys et al. | |
| 6,272,382 B1 | 8/2001 | Faltys et al. | |
| 6,293,945 B1 | 9/2001 | Parins et al. | |
| 6,304,785 B1 * | 10/2001 | McCreery et al. | 607/116 |
| 6,308,101 B1 | 10/2001 | Faltys et al. | |
| 6,321,125 B1 | 11/2001 | Kuzma | |
| 6,421,569 B1 | 7/2002 | Treaba et al. | |
| 6,500,130 B2 | 12/2002 | Gordon et al. | |
| 6,547,762 B1 | 4/2003 | Botich et al. | |
| 6,582,441 B1 | 6/2003 | He et al. | |
| 6,604,283 B1 | 8/2003 | Kuzma | |
| 6,746,412 B1 | 6/2004 | Hill et al. | |
| 6,858,034 B1 | 2/2005 | Hijlkema et al. | |
| 6,866,669 B2 | 3/2005 | Buzzard | |
| 6,936,065 B2 | 8/2005 | Khan et al. | |
| 6,939,352 B2 | 9/2005 | Buzzard et al. | |
| 6,968,238 B1 * | 11/2005 | Kuzma | 607/137 |
| 7,050,858 B1 | 5/2006 | Kuzma et al. | |
| 7,063,708 B2 | 6/2006 | Gibson et al. | |
| 7,269,461 B2 | 9/2007 | Dadd et al. | |
| 7,349,744 B2 | 3/2008 | Dadd et al. | |
| 7,544,197 B2 | 6/2009 | Kelsch et al. | |
| 7,591,268 B2 | 9/2009 | Lowe et al. | |
| 7,792,586 B2 | 9/2010 | Dadd et al. | |
| 7,966,077 B2 | 6/2011 | Risi | |
| 2002/0045927 A1 | 4/2002 | Moore et al. | |
| 2002/0143302 A1 | 10/2002 | Hinchliffe et al. | |
| 2002/0147484 A1 | 10/2002 | Dahl | |
| 2003/0045921 A1 | 3/2003 | Dadd et al. | |
| 2003/0093139 A1 | 5/2003 | Gibson et al. | |
| 2003/0171758 A1 * | 9/2003 | Gibson et al. | 606/129 |
| 2004/0122312 A1 * | 6/2004 | Chesbrough et al. | 600/431 |
| 2004/0127968 A1 | 7/2004 | Kuzma et al. | |
| 2004/0193203 A1 | 9/2004 | Pak et al. | |
| 2004/0220651 A1 | 11/2004 | Kuzma et al. | |
| 2004/0243177 A1 | 12/2004 | Svehla et al. | |
| 2004/0260371 A1 | 12/2004 | Greenland et al. | |
| 2005/0004644 A1 | 1/2005 | Kelsch et al. | |
| 2005/0075606 A1 | 4/2005 | Botich et al. | |
| 2005/0251237 A1 | 11/2005 | Kuzma et al. | |
| 2006/0058861 A1 | 3/2006 | Gibson et al. | |
| 2006/0155353 A1 | 7/2006 | Heil, Jr. | |
| 2006/0241723 A1 * | 10/2006 | Dadd et al. | 607/57 |
| 2007/0043419 A1 | 2/2007 | Nikolchev et al. | |
| 2007/0111175 A1 | 5/2007 | Raven et al. | |
| 2007/0213812 A1 | 9/2007 | Webler et al. | |
| 2007/0233214 A1 | 10/2007 | Chitre et al. | |
| 2008/0004684 A1 | 1/2008 | Dadd et al. | |
| 2008/0082141 A1 | 4/2008 | Risi | |
| 2008/0109011 A1 | 5/2008 | Thenuwara et al. | |
| 2008/0195146 A1 | 8/2008 | Wardle | |
| 2008/0269740 A1 * | 10/2008 | Bonde et al. | 606/53 |
| 2008/0269763 A1 | 10/2008 | Bonde et al. | |
| 2009/0119920 A1 | 5/2009 | Peschke et al. | |
| 2011/0009877 A1 * | 1/2011 | Thenuwara et al. | 606/129 |
| 2011/0301681 A1 | 12/2011 | Risi | |

FOREIGN PATENT DOCUMENTS

| | | |
|---|---|---|
| EP | 1233810 | 8/2002 |
| EP | 1341578 | 9/2003 |
| EP | 1370205 | 12/2003 |
| EP | 1476104 | 11/2004 |
| EP | 2039323 | 3/2009 |
| WO | WO-80/02231 | 10/1980 |
| WO | WO-8900870 | 2/1989 |
| WO | WO-9324058 | 12/1993 |
| WO | WO-95/11710 | 5/1995 |
| WO | WO-9720530 | 6/1997 |
| WO | WO-00/64529 | 11/2000 |
| WO | WO-00/71063 | 11/2000 |
| WO | WO-01/68177 | 9/2001 |
| WO | WO-02/30507 | 4/2002 |
| WO | WO-0230507 | 4/2002 |
| WO | WO-0232498 | 4/2002 |
| WO | WO-02074211 | 9/2002 |
| WO | WO-03/070133 | 8/2003 |
| WO | WO-03070133 | 8/2003 |
| WO | WO-2004/014472 | 2/2004 |
| WO | WO-2004012809 | 2/2004 |
| WO | WO-2005/110529 | 11/2005 |
| WO | WO-2010/045228 A3 | 4/2010 |
| WO | WO-2010/133704 A2 | 11/2010 |
| WO | WO-2011/005993 A1 | 1/2011 |

OTHER PUBLICATIONS

Non-Final Office Action received in U.S. Appl. No. 12/824,119, dated Jun. 8, 2012.

International Search Report and Written Opinion received in International Application No. PCT/US2007/083428 dated May 20, 2008.

International Search Report and Written Opinion received in International Application No. PCT/US2011/041576, dated Sep. 19, 2011.

Non-Final Office Action received in U.S. Appl. No. 12/425,868, dated Nov. 25, 2011.

International Search Report and Written Opinion received in International Application No. PCT/US2011/041577, dated Nov. 30, 2011.

Final Office Action received in U.S. Appl. No. 12/425,868, dated Jul. 6, 2012.

* cited by examiner

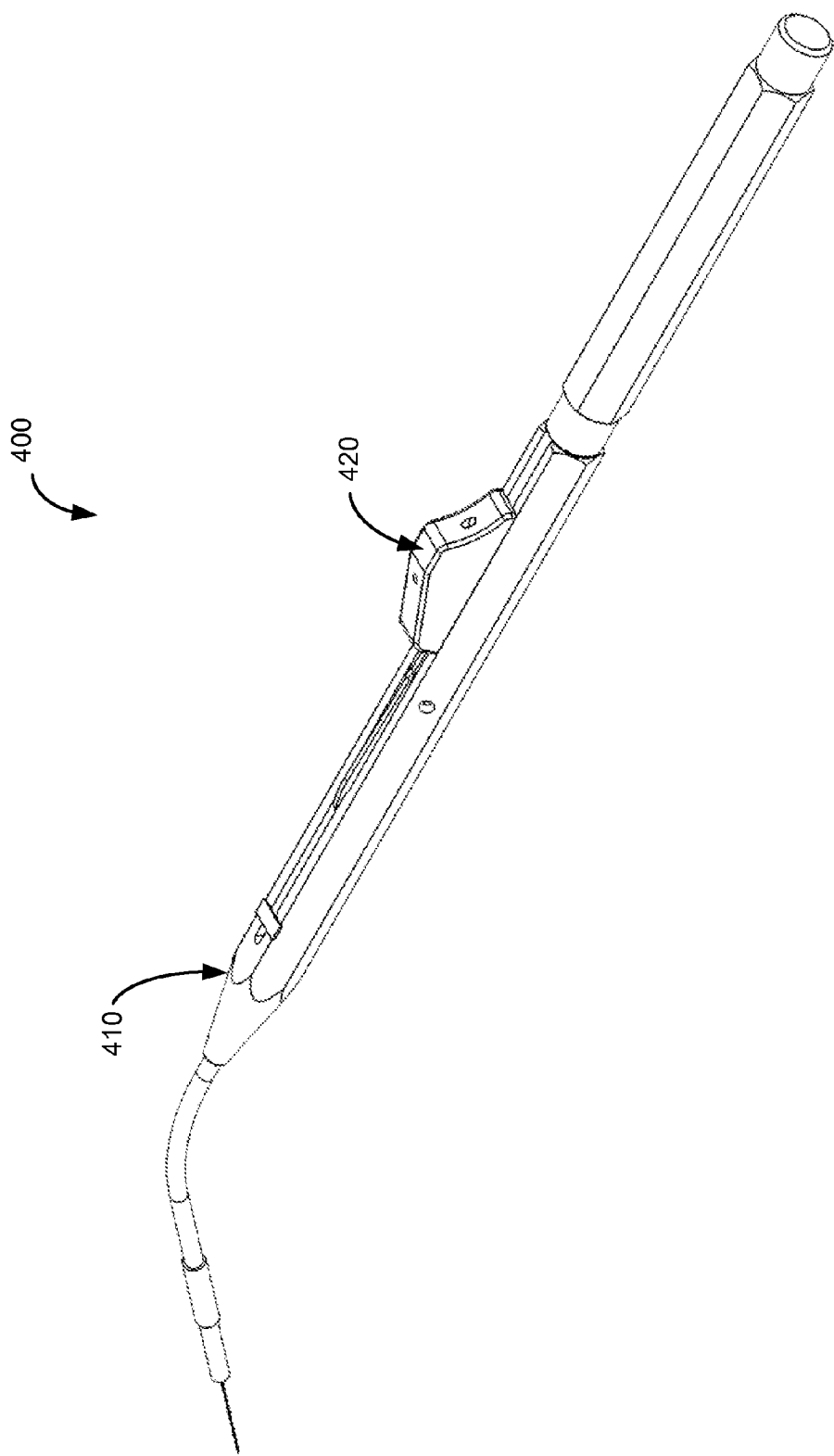

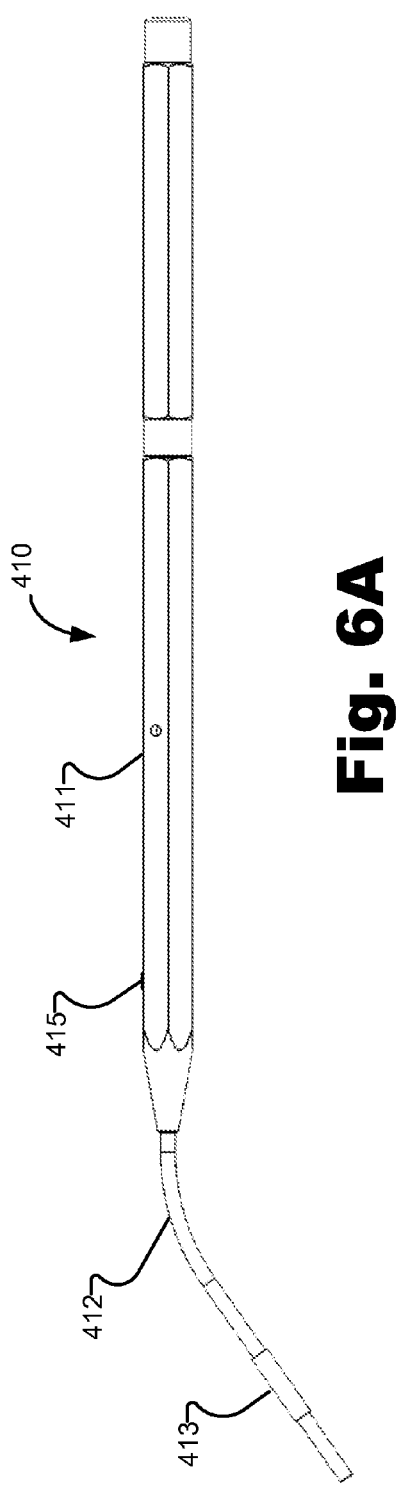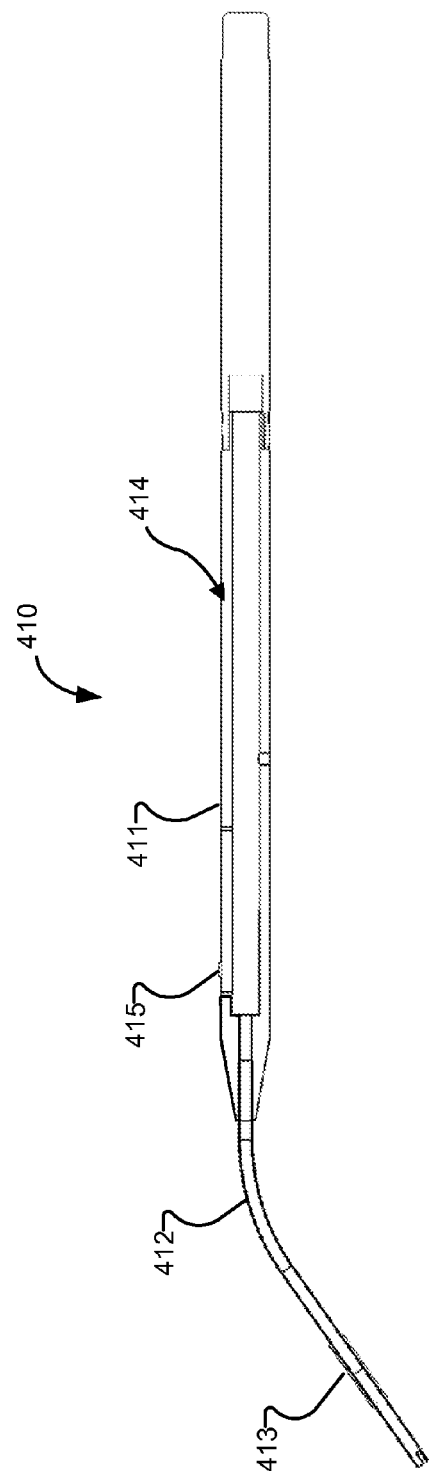

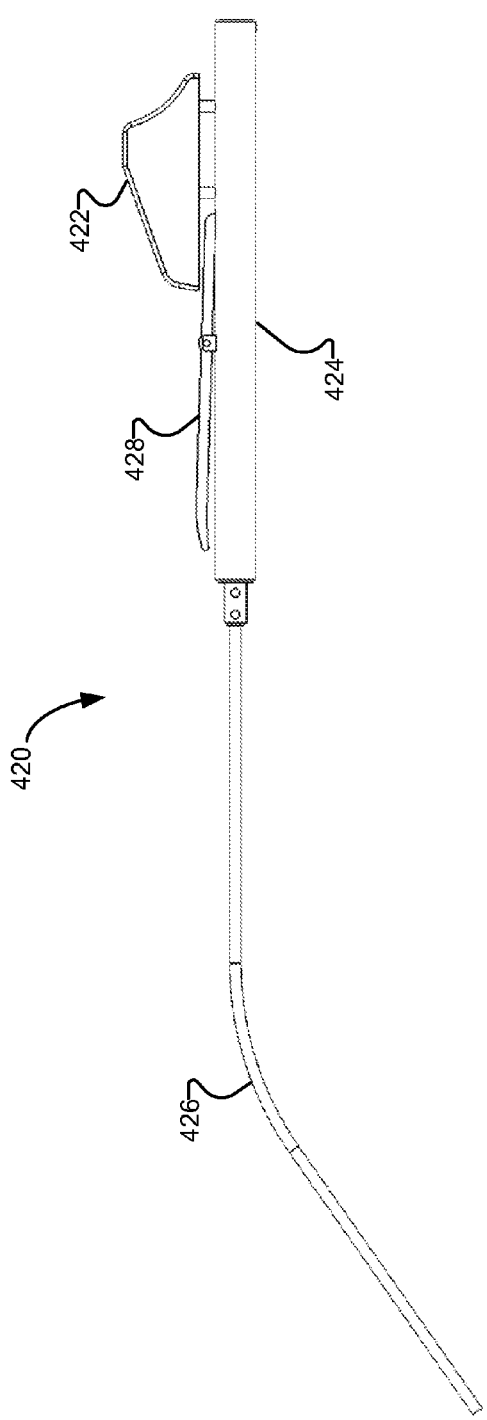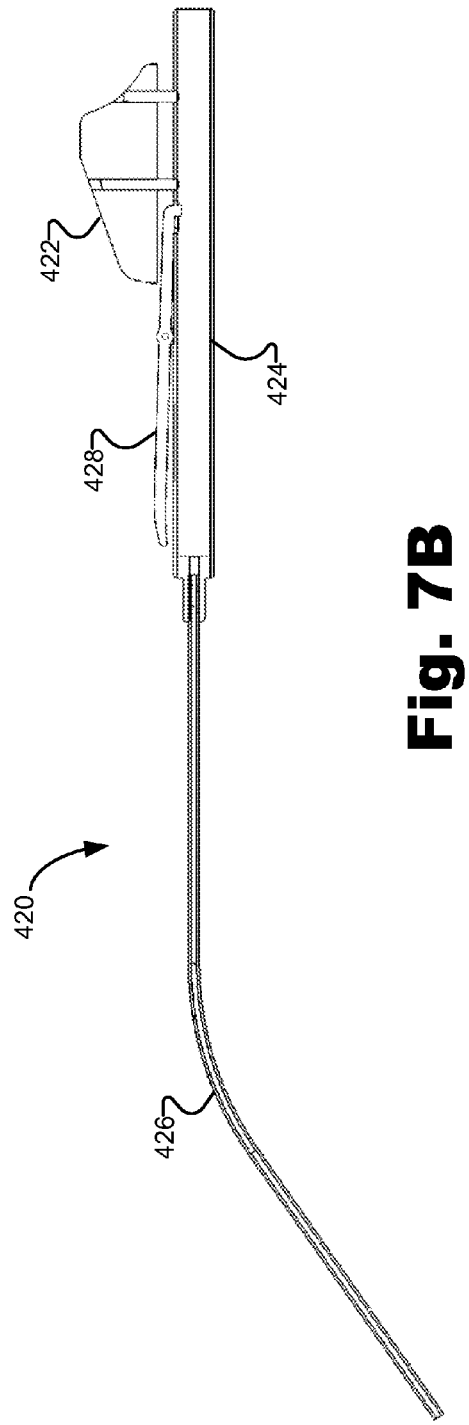
Fig. 7A
Fig. 7B

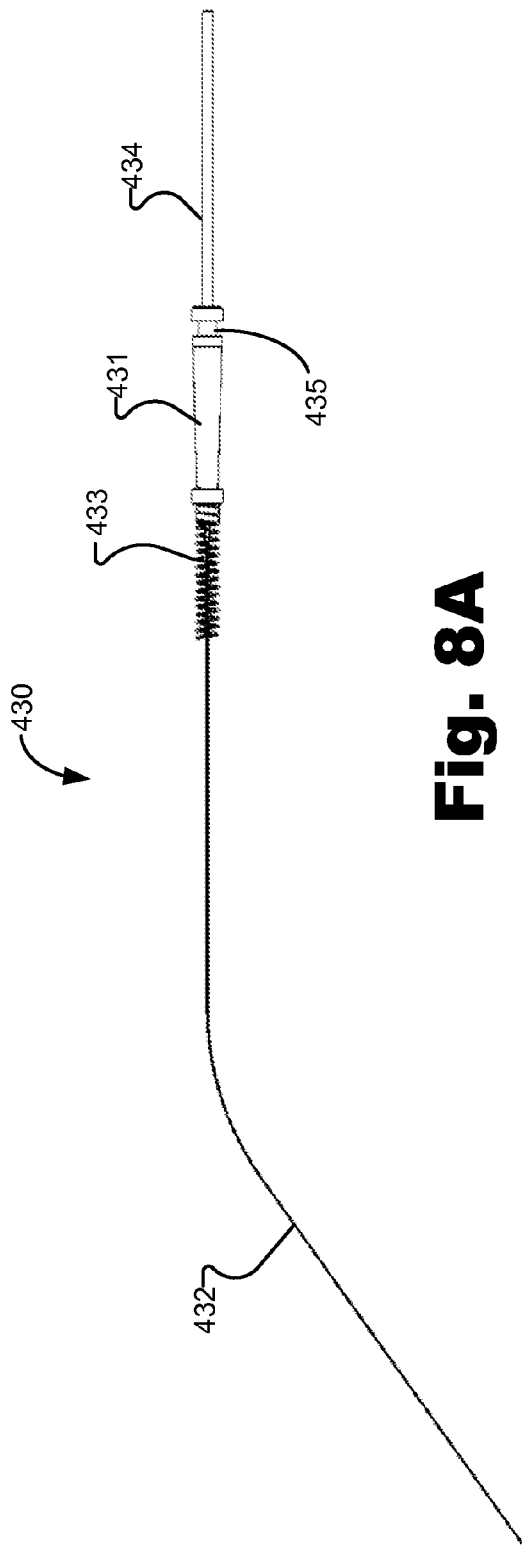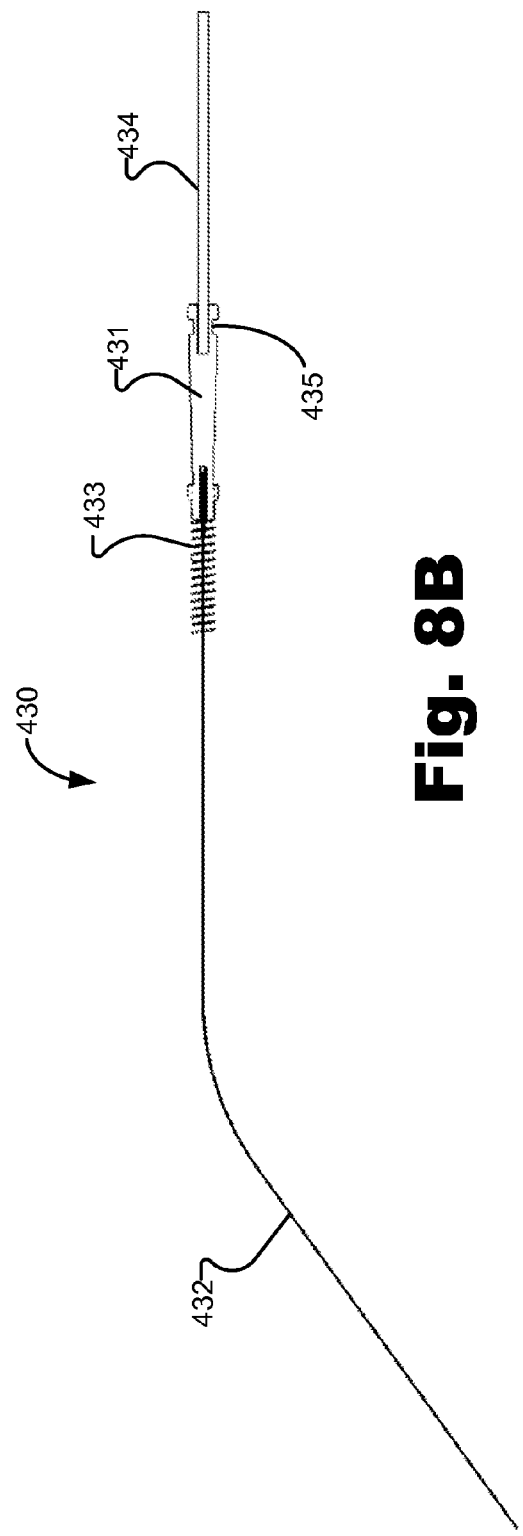

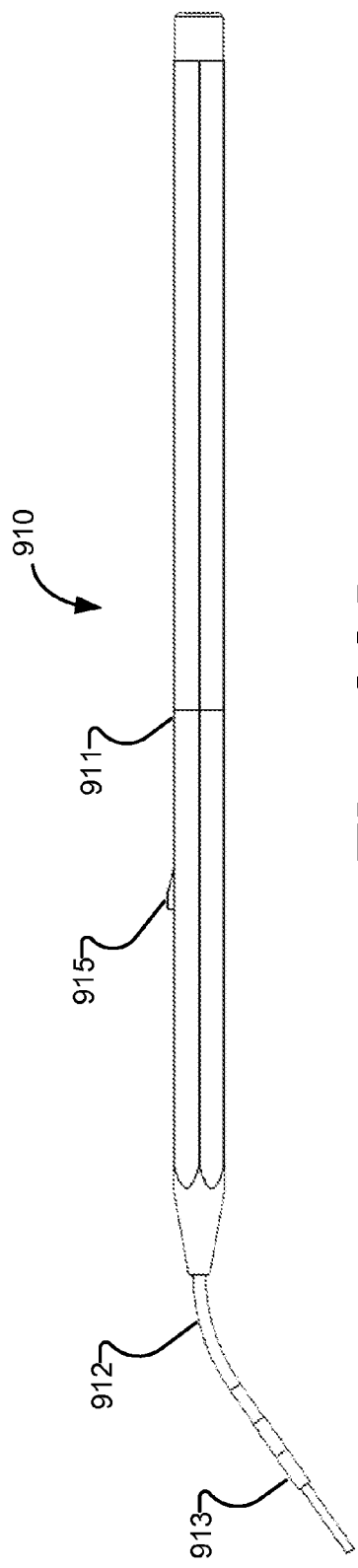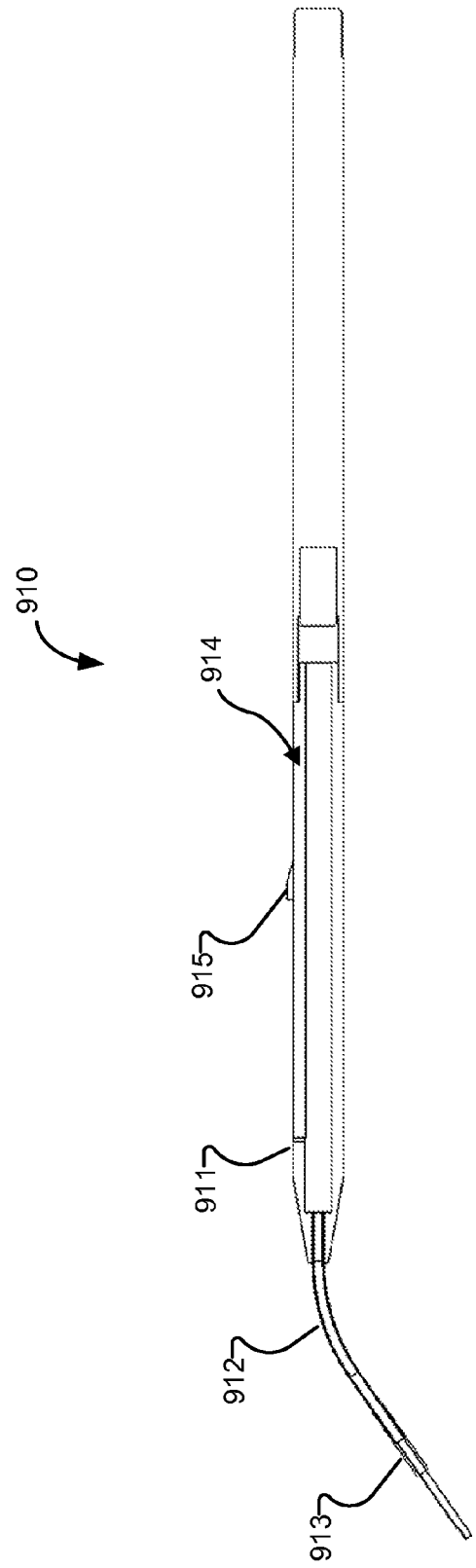

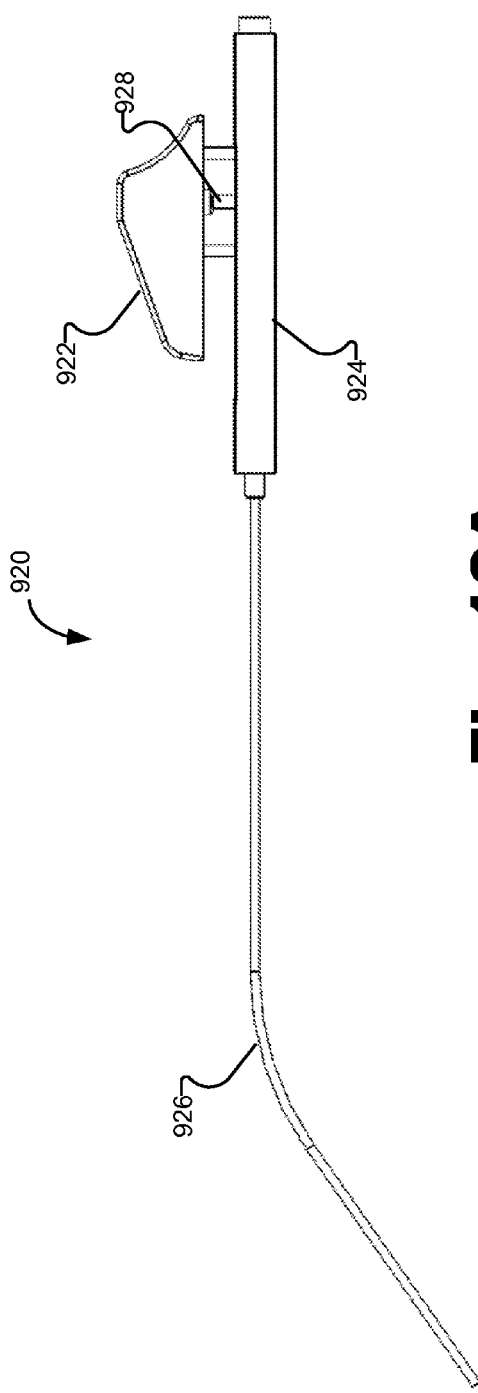
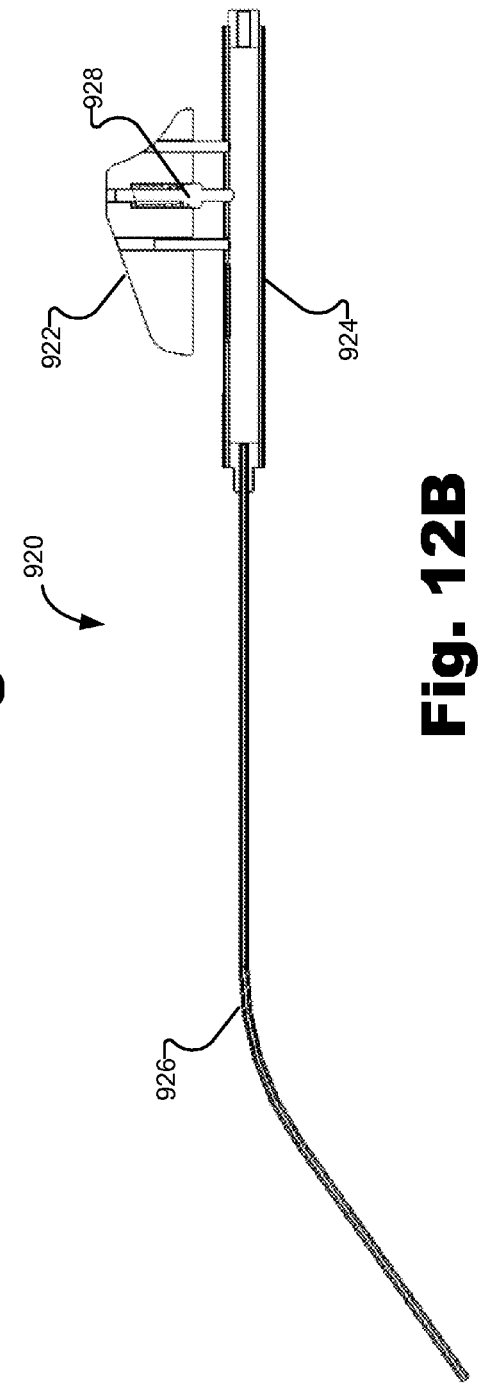

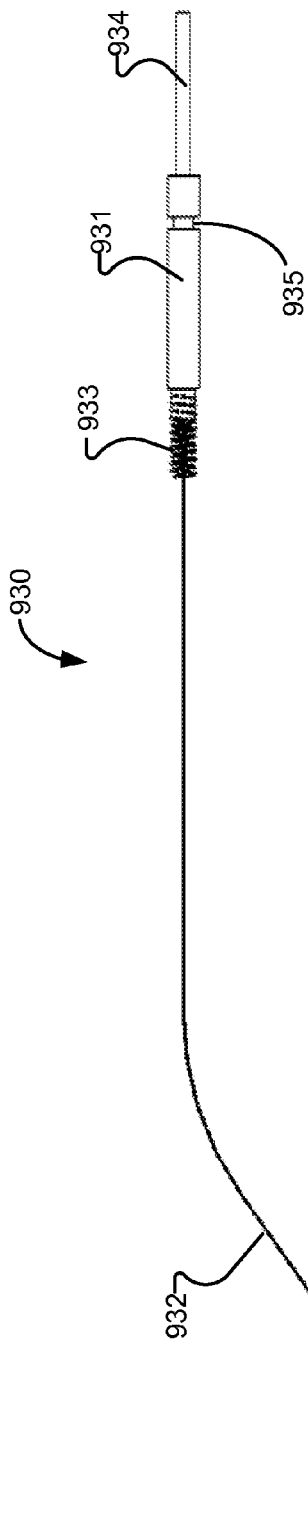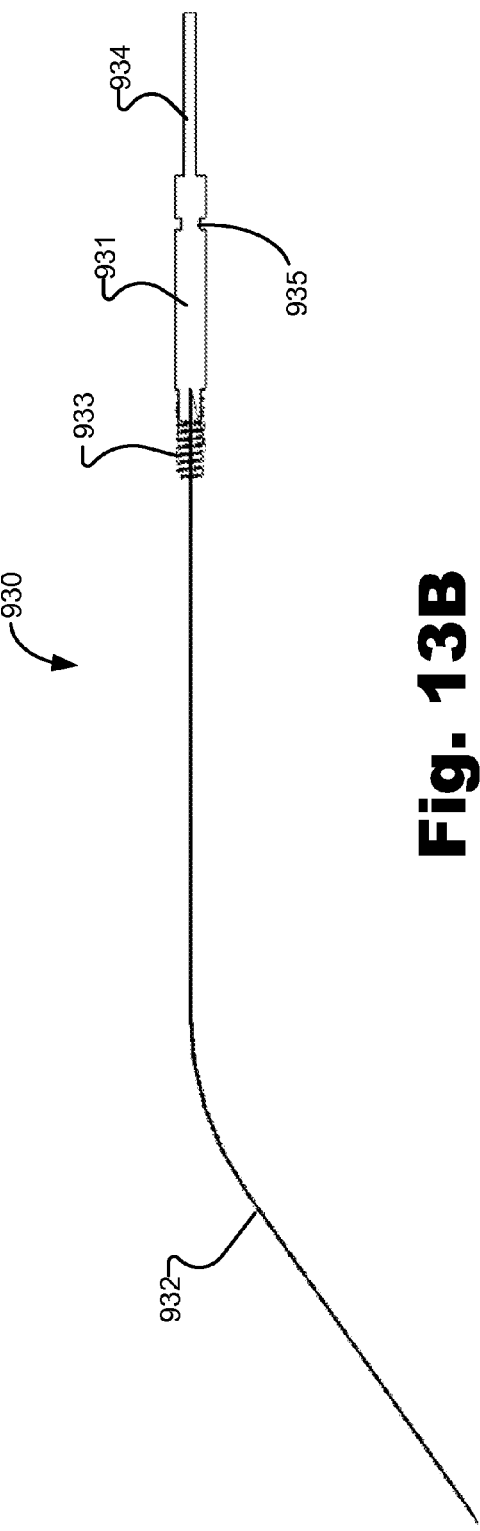

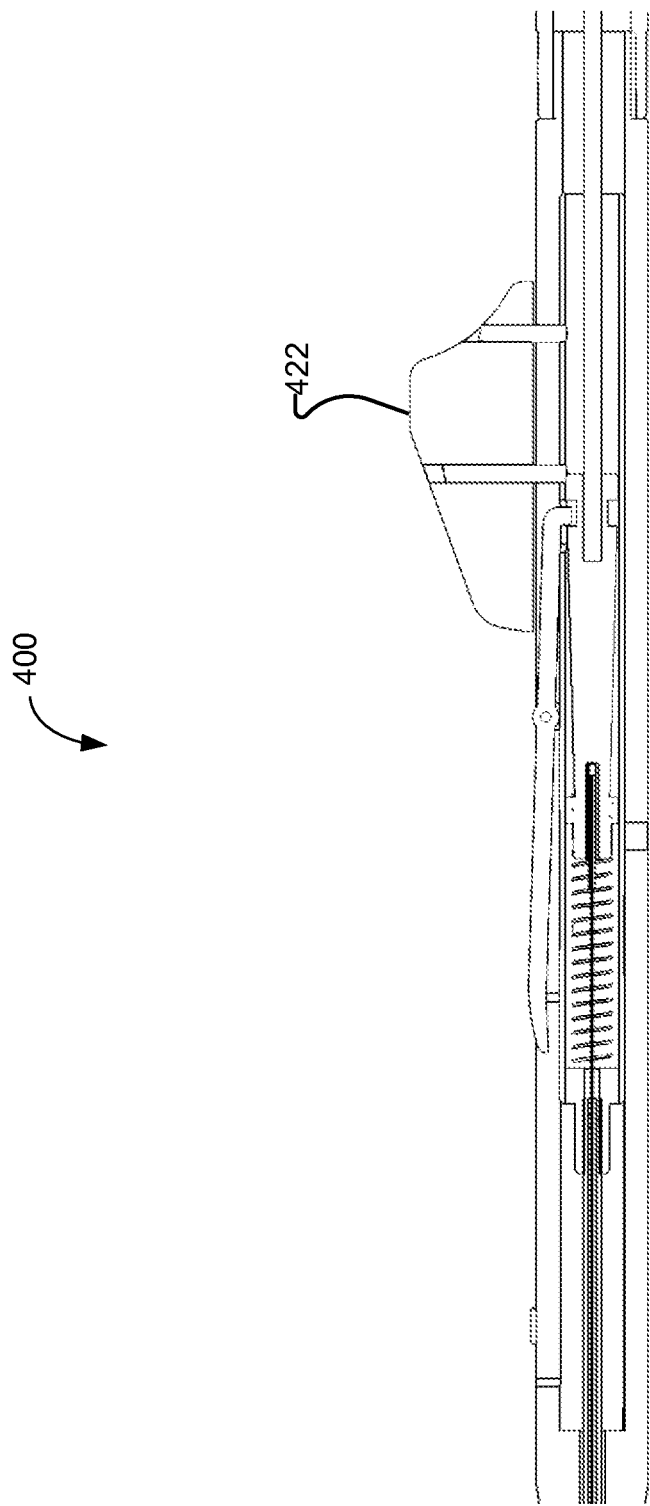

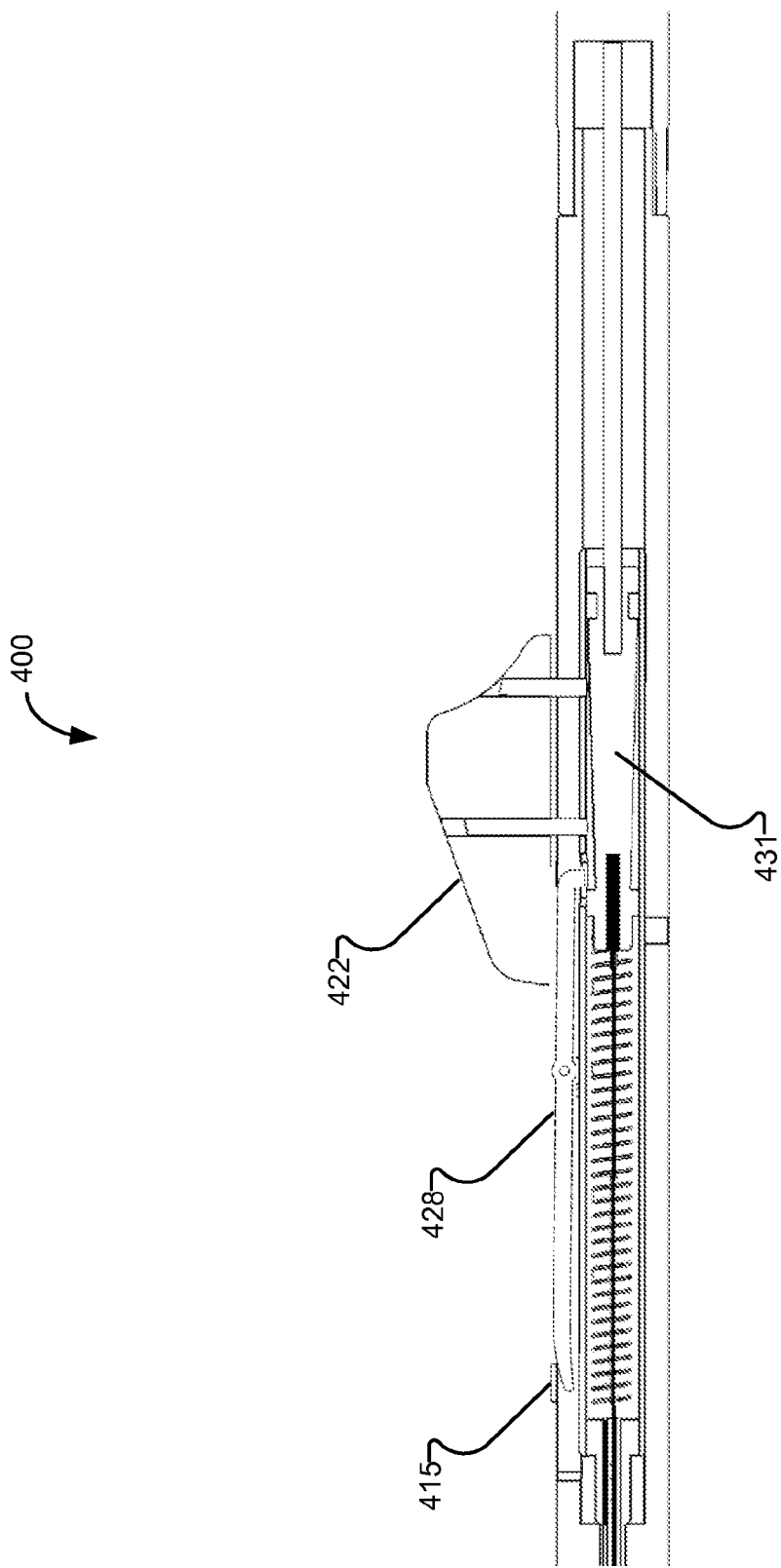

TOOLS, SYSTEMS, AND METHODS FOR INSERTING AN ELECTRODE ARRAY PORTION OF A LEAD INTO A BODILY ORIFICE

BACKGROUND

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an electrode array portion of a lead may be implanted in the cochlea. Electrodes included on the electrode array portion form stimulation channels through which electrical stimulation pulses may be applied directly to auditory nerves within the cochlea. An audio signal may therefore be presented to a patient by translating the audio signal into electrical stimulation pulses and applying the stimulation pulses directly to auditory nerves within the cochlea via one or more of the electrodes.

The electrode array portion is often implanted within the scala tympani, one of three parallel ducts that make up the spiral-shaped cochlea. Electrode array portions that are implanted in the scala tympani typically include several separately connected stimulating electrodes (or "electrode contacts") longitudinally disposed on a thin, elongate, and flexible carrier. Such an electrode array portion is pushed into the scala tympani duct via a surgical opening made in the cochlea wall at or near the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible and/or to any other location (e.g., a mid-scalar location) as may serve a particular application. To this end, various electrode array portions have been developed that have resilient carriers configured to better conform to the shape of the scala tympani and/or other auditory structures.

Unfortunately, many conventional insertion tools used to insert electrode array portions into the cochlea are cumbersome and difficult to use. For example, it is often difficult to release an electrode array portion from an insertion tool once the electrode array portion has been inserted into the cochlea. In addition, a stiffening member (e.g., a stylet) may be used to facilitate insertion of the electrode array portion of a lead into the cochlea, and retracting the stiffening member from the electrode array portion may be difficult and tend to dislodge the electrode array portion out of position.

SUMMARY

An exemplary insertion tool configured to facilitate insertion of a electrode array portion of a lead into a bodily orifice includes a handle assembly, a retractor assembly, and a slider assembly. The handle assembly is configured to facilitate handling of the insertion tool. The retractor assembly is disposed at least partially within the handle assembly and comprises a stiffening member configured to be inserted into the electrode array portion and a spring-loaded retractor member coupled to the stiffening member, which spring-loaded retractor member is configured to move from a distal position to a proximal position to at least partially retract the stiffening member from the electrode array portion. The slider assembly is disposed at least partially within the handle assembly and configured to selectively retain the spring-loaded retractor member relative to the slider assembly. The slider assembly is further configured to release the spring-loaded retractor member to move from the distal position to the proximal position in response to actuation by a user of the slider assembly.

An exemplary system comprises a lead including an electrode array portion and configured to be coupled to an implantable cochlear stimulator, and an insertion tool configured to facilitate insertion of the electrode array portion into a bodily orifice. The insertion tool includes a handle assembly, a retractor assembly, and a slider assembly. The handle assembly is configured to facilitate handling of the insertion tool. The retractor assembly is disposed at least partially within the handle assembly and comprises a stiffening member configured to be inserted into the electrode array portion and a spring-loaded retractor member coupled to the stiffening member, which spring-loaded retractor member is configured to move from a distal position to a proximal position to at least partially retract the stiffening member from the electrode array portion. The slider assembly is disposed at least partially within the handle assembly and configured to selectively retain the spring-loaded retractor member relative to the slider assembly. The slider assembly is further configured to release the spring-loaded retractor member to move from the distal position to the proximal position in response to actuation by a user of the slider assembly.

An exemplary method of inserting an electrode array portion of a lead into a bodily orifice includes guiding the electrode array portion at least partially into a bodily orifice with the insertion tool, moving a slider member of the insertion tool from a first position towards a second position to advance the electrode array portion in a distal direction relative to the handle assembly, and moving the slider member to the second position to release a spring-loaded retractor member to move from a distal position to a proximal position to at least partially retract a stiffening member from the electrode array portion.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 4 is a perspective view of an exemplary insertion tool according to principles described herein.

FIG. 6A is a side view of an exemplary handle assembly of the exemplary insertion tool of FIG. 4 according to principles described herein.

FIG. 6B is a cross-sectional side view of the exemplary handle assembly of FIG. 6A according to principles described herein.

FIG. 7A is a side view of an exemplary slider assembly of the exemplary insertion tool of FIG. 4 according to principles described herein.

FIG. 7B is a cross-sectional side view of the exemplary slider assembly of FIG. 7A according to principles described herein.

FIG. 8A is a side view of an exemplary retractor assembly of the exemplary insertion tool of FIG. 4 according to principles described herein.

FIG. 8B is a cross-sectional side view of the exemplary retractor assembly of FIG. 8A according to principles described herein.

FIG. 11A is a side view of an exemplary handle assembly of the exemplary insertion tool of FIG. 9 according to principles described herein.

FIG. 11B is a cross-sectional side view of the exemplary handle assembly of FIG. 11A according to principles described herein.

FIG. 12A is a side view of an exemplary slider assembly of the exemplary insertion tool of FIG. 9 according to principles described herein.

FIG. 12B is a cross-sectional side view of the exemplary slider assembly of FIG. 12A according to principles described herein.

FIG. 13A is a side view of an exemplary retractor assembly of the exemplary insertion tool of FIG. 9 according to principles described herein.

FIG. 13B is a cross-sectional side view of the exemplary retractor assembly of FIG. 13A according to principles described herein.

FIG. 15C shows a cross-sectional side view of an exemplary slider assembly of the exemplary insertion tool of FIG. 15A in a first position according to principles described herein.

FIG. 15F shows a cross-sectional side view of the exemplary slider assembly in a second position according to principles described herein.

Throughout the drawings, identical reference numbers may designate similar, but not necessarily identical, elements.

DETAILED DESCRIPTION

Exemplary insertion tools, systems, and methods for inserting an electrode array portion of a lead into a bodily orifice are described herein. As used herein, the term "bodily orifice" refers to a duct of the cochlea, a surgically made opening or incision (e.g., a cochleostomy or facial recess) within the patient, or any other location within the patient. For illustrative purposes only, it will be assumed in the examples given that the insertion tools, systems, and methods described herein may be used to insert an electrode array portion of a lead into a duct of the cochlea via a cochleostomy.

In some examples, an exemplary insertion tool described herein includes a handle assembly, a retractor assembly, and a slider assembly. The handle assembly may be configured to facilitate handling of the insertion tool. The retractor assembly may be disposed at least partially within the handle assembly and include a stiffening member configured to be inserted into the electrode array portion and a spring-loaded retractor member configured to move from a distal position to a proximal position to at least partially retract the stiffening member from the electrode array portion. The slider assembly may be disposed at least partially within the handle assembly and configured to selectively retain the spring-loaded retractor member relative to the slider assembly and release the spring-loaded retractor member to move from the distal position to the proximal position in response to actuation by a user of the slider assembly.

A number of advantages are associated with the insertion tools, systems, and methods described herein. For example, the insertion tools described herein may facilitate insertion of an electrode array portion of a lead into a duct of the cochlea.

The insertion tools described herein may additionally or alternatively be used with either the right or left hand of a surgeon or other user to insert an electrode array portion into either a right or left cochlea and are configured to not obstruct the view of the user while inserting the electrode array portion into the cochlea. These and other advantages will be described in more detail below.

In the following description, for purposes of explanation, numerous specific details are set forth in order to provide a thorough understanding of the present tools, systems, and methods. It will be apparent, however, to one skilled in the art that the present tools, systems, and methods may be practiced without these specific details. Reference in the specification to "one embodiment," "an embodiment," "one example," or "an example" means that a particular feature, structure, or characteristic described in connection with the embodiment is included in at least one embodiment. The appearance of the phrase "in one embodiment" in various places in the specification are not necessarily all referring to the same embodiment.

Figure 1:
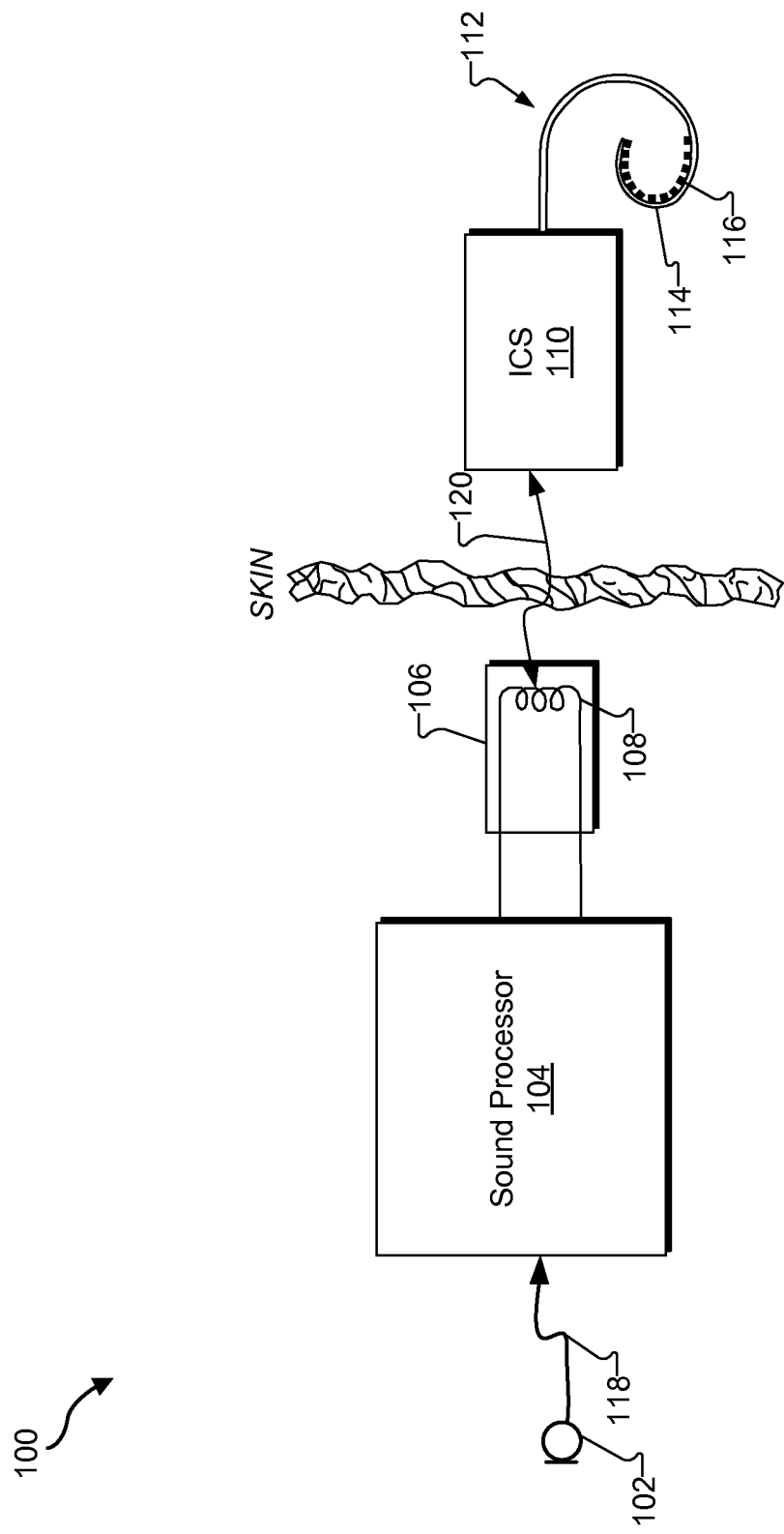
FIG. 1 illustrates an exemplary cochlear implant system according to principles described herein.

FIG. 1 illustrates an exemplary cochlear implant system 100. Cochlear implant system 100 may include a microphone 102, a sound processor 104, a headpiece 106 having a coil 108 disposed therein, an implantable cochlear stimulator ("ICS") 110, and a lead 112 having an electrode array portion 114 that comprises a plurality of electrodes 116. Additional or alternative components may be included within cochlear implant system 100 as may serve a particular application.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 118, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented within a behind-the-ear ("BTE") unit, a portable speech processor ("PSP"), and/or any other sound processing unit as may serve a particular application. Exemplary components of sound processor 104 will be described in more detail below.

Sound processor 104 may be configured to transcutaneously transmit one or more control parameters and/or one or more power signals to implantable cochlear stimulator 110 with coil 108 by way of communication link 120. These control parameters may be configured to specify one or more stimulation parameters, operating parameters, and/or any other parameter as may serve a particular application. Exemplary control parameters include, but are not limited to, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and back-end dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 120. It will be understood that data communication link 120 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 116 of electrode array portion 114 of lead 112.

To facilitate application of the electrical stimulation generated by implantable cochlear stimulator 110, electrode array portion 114 may be inserted within a duct of the cochlea such that electrodes 116 are in communication with one or more stimulation sites within the cochlea. As used herein, the term "in communication with" refers to electrodes 116 being adjacent to, in the general vicinity of, in close proximity to, directly next to, or directly on the stimulation site. Electrode array portion 114 may comprise any number of electrodes 116 (e.g., sixteen) as may serve a particular application.

Figure 2:
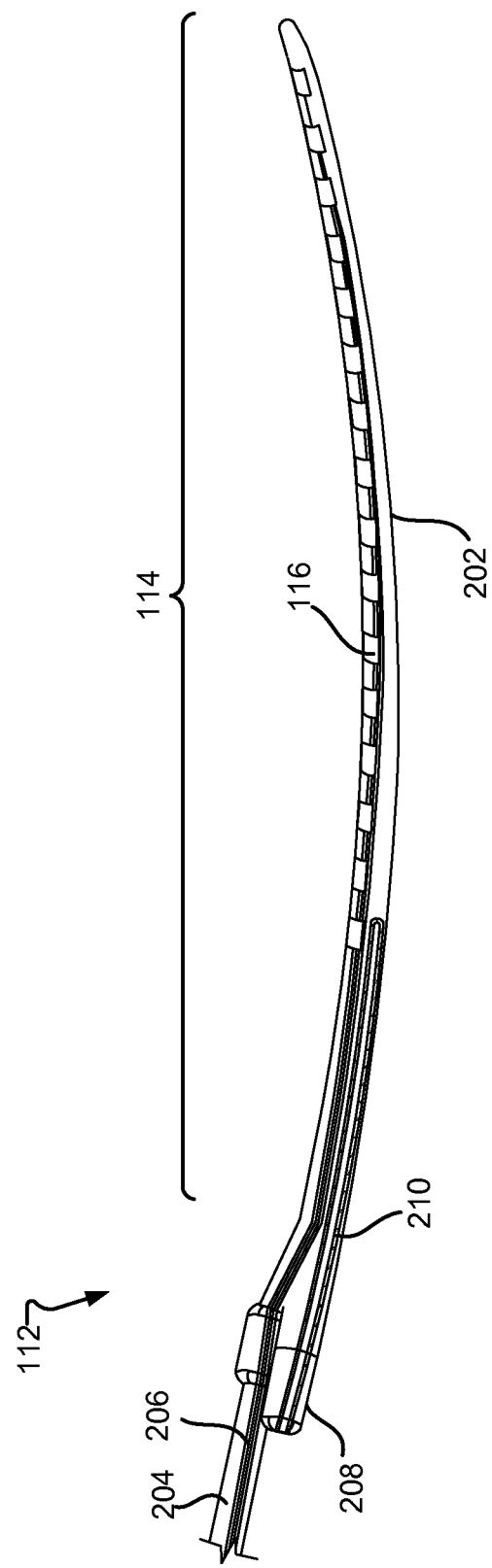
FIG. 2 illustrates an exemplary lead including an electrode array portion according to principles described herein.

FIG. 2 shows a side view of lead 112 including electrode array portion 114. Lead 112 may be substantially as shown and described in U.S. Pat. Nos. 4,819,647; 6,129,753; or 6,604,283, and in the U.S. patent application entitled "COCHLEAR IMPLANT SYSTEM WITH REMOVABLE STYLET" to Gallegos et al. filed Jun. 25, 2010 and having attorney docket number 09-00048-01, each of which is incorporated herein by reference in its respective entirety.

As shown, in some examples, lead 112 may include electrode array portion 114 having an array of electrodes 116 disposed on an elongate flexible carrier 202 (or simply "carrier 202"), a lead body 204 connected to a proximal end of carrier 202, insulated wires 206 disposed through lead body 204 (e.g., to connect electrodes 116 to implantable cochlear stimulator 110), and a molded feature 208 coupled to a proximal end of carrier 202 and configured to provide a structure that can couple to an insertion tool.

Elongate flexible carrier 202 may be made out of any suitable material such as, but not limited to, medical grade silicone rubber or plastic, and may include a lumen 210 passing at least partially therethrough. In some examples, carrier 202 may be tapered such that a distal portion (e.g., the portion common with electrode array portion 114) is thinner and, as a result, more flexible than a proximal portion. Carrier 202 may be configured to allow electrode array portion 114 to bend and conform to the geometry of a cochlea. In some examples, electrodes 116 of electrode array portion 114 may be configured to be positioned along a medial electrode wall (e.g., along the inside curve of carrier 202) such that they face the modiolus when implanted in the cochlea. Accordingly, electrode array portion 114 may be inserted into the scala tympani of the cochlea, thereby bringing electrodes 116 into close proximity with the auditory nerve tissue of the cochlea.

Lumen 210 may have any suitable length and may extend at least partially through carrier 202 and/or electrode array portion 114 to any of a variety of locations. In some examples, lumen 210 may be configured to receive a stiffening member (e.g., a stylet) to facilitate insertion of electrode array portion 114 into a cochlea, as will be explained in more detail below.

Figure 3:
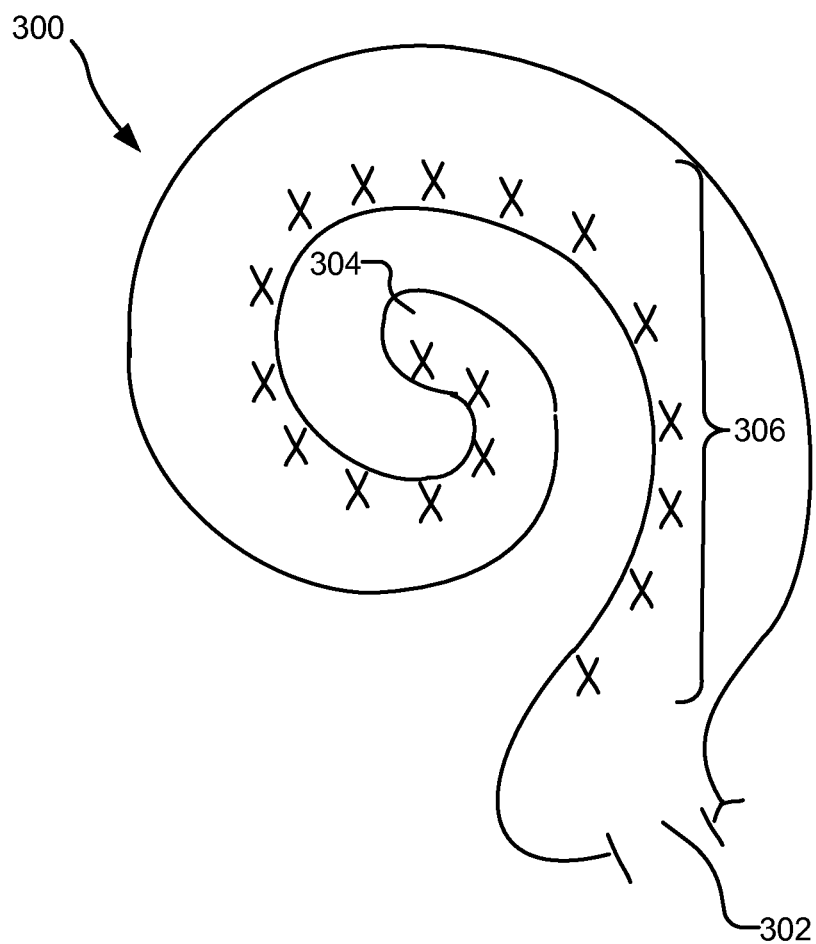
FIG. 3 illustrates a schematic structure of a human cochlea.

FIG. 3 illustrates a schematic structure of the human cochlea 300 into which electrode array portion 114 may be inserted. As shown in FIG. 3, the cochlea 300 is in the shape of a spiral beginning at a base 302 and ending at an apex 304. Within the cochlea 300 resides auditory nerve tissue 306, which is denoted by Xs in FIG. 3. The auditory nerve tissue 306 is organized within the cochlea 300 in a tonotopic manner. Low frequencies are encoded at the apex 304 of the cochlea 300 while high frequencies are encoded at the base 302. Hence, each location along the length of the cochlea 300 corresponds to a different perceived frequency. System 100 may therefore be configured to apply electrical stimulation to different locations within the cochlea 300 (e.g., different locations along the auditory nerve tissue 306) to provide a sensation of hearing.

Figure 5A:
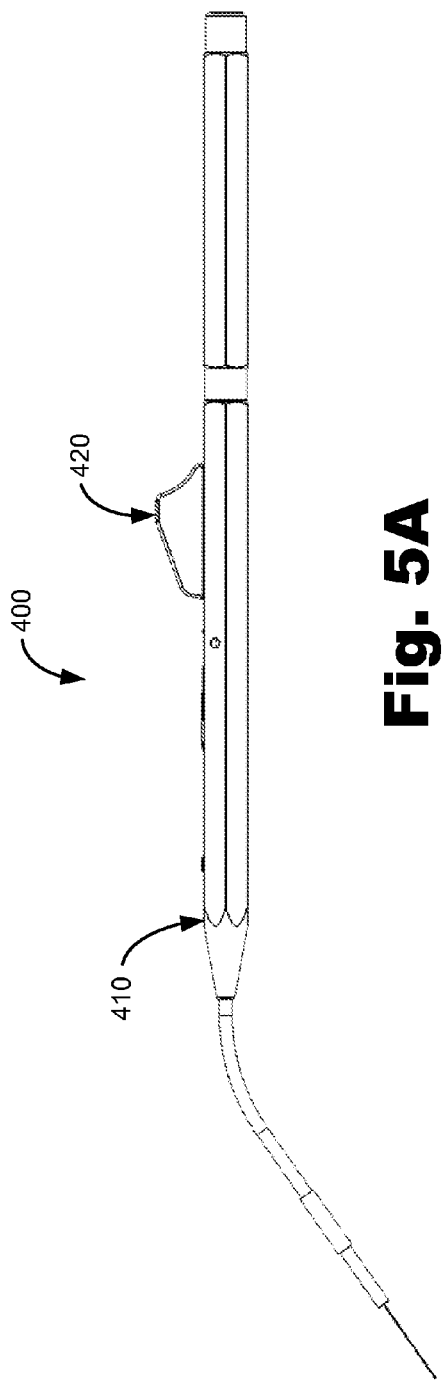
FIG. 5A is a side view of the exemplary insertion tool of FIG. 4 according to principles described herein.
Figure 5B:
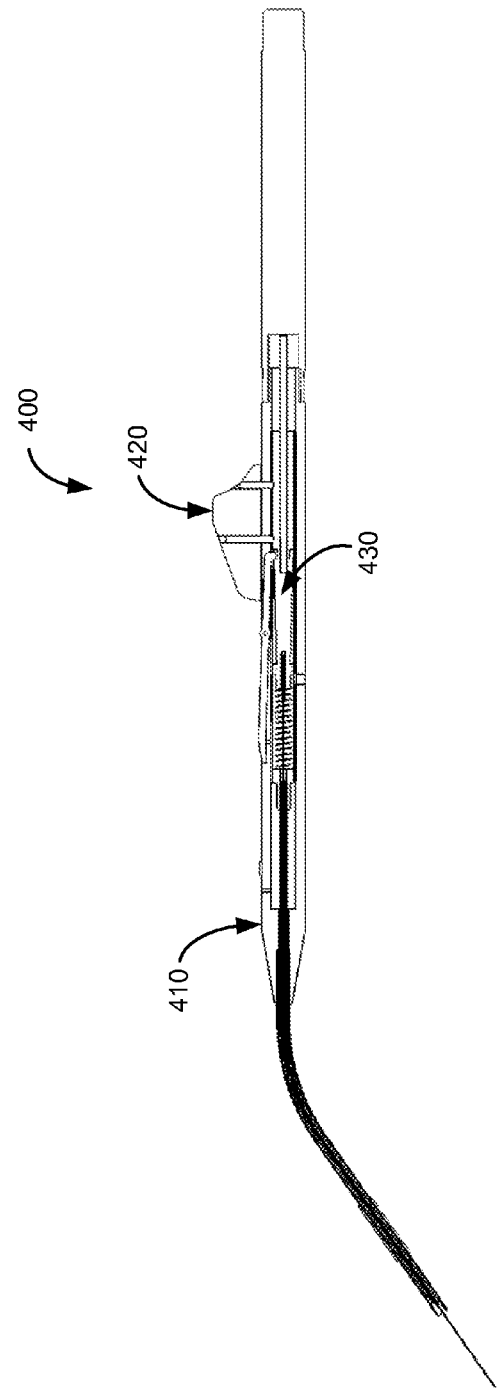
FIG. 5B is a cross-sectional side view of the exemplary insertion tool of FIG. 4 according to principles described herein.

FIG. 4 is a perspective view of an exemplary insertion tool 400 configured to facilitate insertion of an electrode array portion of a lead into a bodily orifice according to principles described herein. FIG. 5A is a side-view of insertion tool 400, and FIG. 5B is a cross-sectional side view of insertion tool 400. As shown, insertion tool 400 may include a handle assembly 410, a slider assembly 420 disposed at least partially within and slidable relative to handle assembly 410, and a retractor assembly 430 disposed at least partially within handle assembly 410 and/or slider assembly 420. Each of the components of insertion tool 400 and the interaction between the components of insertion tool 400 will now be described in more detail.

As mentioned above, insertion tool 400 may include handle assembly 410. Handle assembly 410 may be configured to facilitate handling of insertion tool 400 by a user (e.g., a surgeon) and/or contain one or more other components of insertion tool 400. Handle assembly 410 is shown in more detail in FIG. 6A, which illustrates a side view of handle assembly 410, and FIG. 6B, which illustrates a cross-sectional side view of handle assembly 410.

As shown, handle assembly 410 may include a handle portion 411, a guide tube 412 coupled to a distal end of handle portion 411, and a holder member 413 coupled to a distal end of guide tube 412. Handle portion 411 may be configured to be gripped and/or handled by a user (e.g., a surgeon) of insertion tool 400 and may house one or more other components of insertion tool 400. In some examples, handle portion 411 may have a hexagonal cross-section to facilitate optimal gripping thereof by a user. Handle portion 411 may have a generally elongate shape and may be generally tubular with a lumen extending at least partially therethrough. In this manner, one or more other components of insertion tool 400 (e.g., slider assembly 420 and/or retractor assembly 430) may be disposed at least partially within and/or slide relative to handle portion 411, as will be explained in more detail below.

Handle portion 411 may include one or more other features configured to facilitate coupling and/or interaction between handle portion 411 and one or more other components of insertion tool 400. For example, handle portion 411 may include a handle slot 414 extending along a length thereof and configured to allow one or more components of insertion tool to extend through handle slot 414 and/or move relative to handle portion 411 within handle slot 414. In certain examples, a portion of slider assembly 420 may pass through handle slot 414 and may be configured to slide along handle slot 414 relative to handle portion 411 to facilitate actuation of slider assembly 420 by a user.

Guide tube 412 may be coupled to a distal end of handle portion 411. Guide tube 412 may be coupled to handle portion 411 in any suitable manner as may serve a particular implementation. For example, guide tube 412 may be welded, glued, or otherwise coupled to handle portion 411. Alternatively, guide tube 412 and handle portion 411 may be integrally formed together.

Guide tube 412 may be configured to at least partially contain one or more other components of insertion tool 400. For example, guide tube 412 may include a lumen extending along at least a length thereof and in communication with the lumen of handle portion 411. In some examples, portions of slider assembly 420 and/or retractor assembly 430 may be at least partially disposed within and slidable relative to guide tube 412, as will be described in more detail below.

As shown, guide tube 412 may include a curved portion such that a distal portion of guide tube 412 extends away from handle portion 411 at a predefined angle. Guide tube 412 may extend away from handle portion 411 at any suitable angle (e.g., approximately 45 degrees) as may serve a particular implementation. In certain embodiments, the angle of guide tube 412 may prevent handle portion 411 from obscuring the view of a user (e.g., a surgeon) as the user utilizes insertion tool 400 to insert an electrode array portion into a bodily orifice.

Holder member 413 may be configured to couple to a distal end of guide tube 412. For example, a proximal portion of holder member 413 may be configured to receive and couple to a distal portion of guide tube 412. Additionally or alternatively, holder member 413 may be configured to be rotatable relative to guide tube 412. Accordingly, a user may rotate holder member 413 relative to guide tube 412 as desired to facilitate the selective use of insertion tool 400 to insert an electrode array portion into a right or left cochlea.

In some examples, holder member 413 may be configured to removably couple to a lead. For example, holder member 413 may include a lumen extending therethrough with a distal portion configured hold a portion of a lead proximal of the electrode array portion of the lead (e.g., molded feature 208). The lumen of holder member 413 may be in communication with the lumen of guide tube 412. Additionally or alternatively, holder member 413 may include a distal slot within a distal end thereof configured to hold a portion of a lead proximal of the electrode array portion of the lead (e.g., molded feature 208). In some examples, the distal slot may be configured to hold the lead and prevent relative rotation between holder member 413 and the lead.

A striker plate 415 may be coupled to handle portion 411 and may be configured to engage a portion of slider assembly 420. For example, striker plate 415 may extend over handle slot 414 and may be configured to engage a portion of slider assembly 420 as slider assembly 420 moves within handle slot 414 from a first position to a second position, as will be explained in more detail below.

Handle portion 411, guide tube 412, holder member 413, and/or striker plate 415 may be made out of any rigid material as may serve a particular implementation. For example, handle portion 411, guide tube 412, holder member 413, and/or striker plate 415 may be made out of stainless steel, titanium, a hard plastic, any other suitable material, and/or combinations thereof as may serve a particular implementation.

Handle portion 411, guide tube 412, holder member 413, and striker plate 415 are provided for illustrative purposes only and are not limiting. Handle assembly 410 may include additional or alternative elements and/or may exclude certain illustrated elements according to principles described herein.

Returning to FIGS. 4, 5A, and 5B, insertion tool 400 may include slider assembly 420 disposed at least partially within and slidable relative to handle assembly 410. Slider assembly 420 may be configured to be actuated by a user to operate insertion tool 400. For example, slider assembly 420 may be configured to be actuated by a user to advance an electrode array portion of a lead relative to handle assembly 410 and/or to at least partially retract a stiffening member from the electrode array portion.

Slider assembly 420 is shown in greater detail in FIG. 7A, which illustrates a side view of slider assembly 420, and FIG. 7B, which illustrates a cross-sectional side view of slider assembly 420. As shown, slider assembly 420 may include a slider member 422, a slider housing 424 coupled to slider member 422, a tubular member 426 coupled to a distal end of slider housing 424, and/or a rocker lever 428 pivotably coupled to slider housing 424.

Slider member 422, slider housing 424, and/or tubular member 426 may be coupled together in any suitable manner as may serve a particular implementation. For example, slider member 422, slider housing 424, and/or tubular member 426 may be welded, glued, or otherwise coupled together. Alternatively, slider member 422, slider housing 424, and/or tubular member 426 may be integrally formed together. Rocker lever 428 may be coupled to slider housing 424 in any suitable manner that allows rocker lever 428 to pivot relative to slider housing 424.

Slider member 422 may be configured to be actuated (e.g., advanced in a distal direction relative to handle assembly 410) by a user to perform one or more of the functions of insertion tool 400 described herein. For example, slider member 422 may be at least partially disposed within and slidable relative to handle portion 411. In certain embodiments, a portion of slider member 422 may be disposed within the lumen of handle portion 411 while another portion of slider member 422 may extend through handle slot 414 and out of handle portion 411 to facilitate actuation of slider member 422 by a user.

Slider member 422 may include one or more features configured to facilitate actuation by a user. For example, slider member 422 may include grooves or ridges disposed along a surface thereof configured to promote friction between a user's fingers or thumb and slider member 422. Additionally or alternatively, the shape of slider member 422 may conform to the shape of a user's finger or thumb to facilitate gripping and actuation of slider member 422. Slider member 422 may include any other features configured to facilitate actuation of slider member 422 by a user as may be suitable for a particular implementation.

In some examples, slider member 422 may be configured to slide relative to handle assembly 410 between a first position and a second position. A user may selectively actuate slider member 422 to move slider member from the first position to the second position to perform one or more operations of the insertion tool 400. For example, a user may move slider member 422 from a first position to a second position to advance slider housing 424, tubular member 426, and/or rocker lever 428 in a distal direction relative to handle assembly 410. In some examples, moving slider member 422 from the first position to the second position may cause rocker lever 428 to engage striker plate 415. Additionally or alternatively, moving slider member 422 from the first position towards the second position may cause tubular member 426 to engage and advance an electrode array portion of a lead in a distal direction relative to handle assembly 410. In certain embodiments, moving slider member 422 from the first position towards the second position may advance one or more components of retractor assembly 430 in a distal direction relative to handle assembly, as will be explained in more detail below.

Slider member 422 may be configured to provide tactile feedback to a user. For example, slider member 422 may be configured to engage a detent (e.g., within or extending from handle portion 411) configured to resist movement of slider member 422 from the first position. As a result, engagement of the detent by slider member 422 may allow a user to feel when slider member 422 is in the first position. Additionally or alternatively, engagement of striker plate 415 by rocker lever 428 may allow the user to feel when slider member 422 is in the second position.

Slider housing 424 may be configured to house one or more other components of insertion tool 400. For example, slider housing 424 may include a lumen extending therethrough, within which one or more other components of insertion tool 400 may be disposed. In some examples, retractor assembly 430 may be at least partially disposed within and slidable relative to slider housing 424, as will be explained in more detail below.

Slider member 422 and/or slider housing 424 may be made out of any suitable materials as may serve a particular implementation. For example, slider member 422 and/or slider housing 424 may be made out of one or more rigid materials, such as stainless steel, titanium, a hard plastic, any other suitable material, or combinations thereof.

Tubular member 426 may be coupled to a distal end of slider member 422 and extend in a distal direction away from slider member 422. Tubular member 426 may be configured to contain one or more other components of insertion tool 400. For example, tubular member 426 may include a lumen extending therethrough and in communication with the lumen of slider member 422. In some examples, retractor assembly 430 may be disposed at least partially within and slidable relative to tubular member 426, as will be explained in more detail below.

In some examples, tubular member 426 may be configured to be disposed within and slidable relative to handle assembly 410. For example, tubular member 426 may be configured to extend through at least a portion of guide tube 412. In certain examples, tubular member 426 may be configured to extend beyond a distal end of guide tube 412 in response to actuation by a user of slider member 522.

Tubular member 426 may be made out of any suitable material as may serve a particular implementation. For example, tubular member 426 may be made out of one or more semi-rigid or flexible materials, such as PTFE or any other suitable material as may serve a particular implementation.

A distal end of tubular member 426 may be configured to engage and push on a portion of a lead. For example, tubular member 426 may be configured to advance lead 112 to advance electrode array portion 114 in a distal direction relative to handle assembly 410 and/or into a human cochlea, as will be described in more detail below.

Tubular member 426 may be configured to contain one or more other components of insertion tool 400. For example, tubular member 426 may include a lumen extending therethrough and in communication with the lumen of slider housing 424. In some examples, retractor assembly 430 may be disposed at least partially within and slidable relative to tubular member 426, as will be explained in more detail below.

Tubular member 426 may be made out of any suitable material as may serve a particular implementation. For example, tubular member 426 may be made out of one or more semi-rigid or flexible materials, such as polytetrafluoroethylene ("PTFE") or any other suitable material as may serve a particular implementation.

Rocker lever 428 may be configured to selectively engage one or more components of retractor assembly 430 to retain retractor assembly 430 relative to slider assembly 420 and, in response to actuation by a user of slider member 522, release retractor assembly 430 as will be explained in more detail below.

In some examples, rocker lever 428 may be generally elongate in shape and may be configured to pivot relative to slider housing 424. Rocker lever 428 may include a distal portion configured to engage striker plate 515. For example, the distal portion may be configured to extend upwards out of handle slot 414 of handle portion 511 to engage striker plate 515. Rocker lever 428 may include a proximal portion configured to engage one or more components of retractor assembly 430. For example, the proximal portion of rocker lever 428 may include a bend extending away from a longitudinal axis of rocker lever 428 at approximately a right angle and may be configured to engage one or more components of retractor assembly 430 and retain retractor assembly 430 relative to slider assembly 420.

Rocker lever 428 may include an axle and may be configured to pivot about the axle. As a result, rocker lever 428 may pivot in a first direction to engage retractor assembly 430 with the proximal portion of rocker lever 428 to retain retractor assembly 430 relative to slider assembly 420. Additionally or alternatively, rocker lever 428 may be configured to engage striker plate 415 with the distal portion of rocker lever 428 and, in response to engagement of striker plate 415, pivot in a second direction opposite the first direction causing the proximal portion of rocker lever 428 to disengage and release retractor assembly 430, as will be explained in more detail below.

Rocker lever 428 may be made out of any suitable material as may serve a particular implementation. For example, rocker lever 428 may be made out of one or more rigid materials, such as stainless steel, titanium, a rigid plastic, any other suitable rigid material, or combinations thereof as may serve a particular implementation.

Slider member 422, slider housing 424, tubular member 426, and rocker lever 428 are provided for illustrative purposes only and are not limiting. One will appreciate that slider assembly 420 may include additional or alternative elements and/or may exclude certain illustrated elements according to principles described herein.

Returning to FIG. 5B, as shown, insertion tool 400 may include retractor assembly 430 disposed at least partially within and slidable relative to handle assembly 410 and/or slider assembly 420. As will be explained in more detail below, retractor assembly 430 may be configured to include a stiffening member configured to be inserted into an electrode array portion of a lead and at least partially retract the stiffening member from the electrode array portion in response to actuation by a user of slider assembly 420.

Retractor assembly 430 is shown in greater detail in FIG. 8A, which illustrates a side view of retractor assembly 430, and FIG. 8B, which illustrates a cross-sectional side view of retractor assembly 430. As shown, retractor assembly 430 may include a retractor member 431, a stiffening member 432 coupled to and extending from a distal end of retractor member 431, a spring member 433 coupled to retractor member 431, and a backstop 434 coupled to a proximal end of retractor member 431.

Retractor member 431, stiffening member 432, spring member 433, and/or backstop 434 may be coupled together in any suitable manner as may serve a particular implementation. For example, retractor member 431, stiffening member 432, spring member 433, and/or backstop 434 may be welded, glued, or otherwise coupled together. Alternatively, retractor member 431, stiffening member 432, spring member 433, and/or backstop 434 may be integrally formed together.

Stiffening member 432 may be configured to insert at least partially into an electrode array portion of a lead (e.g., into electrode array portion 114 of lead 112) to assist in the insertion of the electrode array portion into a cochlea. For example, a distal end of stiffening member 432 may be configured to be inserted into a lumen within the electrode array portion to provide sufficient stability to insert the electrode array portion into the cochlea. In some examples, stiffening member 432 may be configured to include and/or have the characteristics of a stylet.

Stiffening member 432 may be made out of any suitable material with sufficient stiffness so as to facilitate entry of an electrode array portion into the cochlea. For example, stiffening member 432 may be made out of a metal (e.g., stainless steel or titanium), a metal alloy, a hard plastic, any other suitable material, and/or combinations thereof.

As shown, stiffening member 432 may be fixedly coupled to a distal end of retractor member 431. However, in alternative examples, stiffening member 432 and retractor member 431 may be configured to be removably coupled together such that a user may choose to uncouple and/or re-couple stiffening member 432 and retractor member 431 as may be suitable for a particular implementation.

Retractor member 431 may be configured to slide relative to handle assembly 410 and/or slider assembly 420 to at least partially retract stiffening member 432 from an electrode array portion of a lead. For example, retractor member 431 may be configured to be slidable relative to handle assembly 410 and/or slider assembly 420 from a distal position to a proximal position to at least partially retract stiffening member 432 from the electrode array portion.

In some examples, retractor member 431 may be configured to move from the distal position to the proximal position in response to actuation by a user of slider assembly 420. For example, retractor member 431 may be retained relative to slider assembly by rocker lever 428 and then released when rocker lever 428 engages striker plate 415. While retractor member 431 is retained relative to slider assembly 420, spring member 433 may be configured to store sufficient energy (e.g., in a compressed position) to move retractor member 431 from the distal position to the proximal position. Upon release of retractor member 431, spring member 433 may release the stored energy (e.g., elongate) to move retractor member 431 from the distal position to the proximal position. As a result, retractor member 431 may at least partially retract stiffening member 432 from the electrode array portion. In some examples, a distal end of spring member 433 may be coupled to slider assembly 420 to facilitate movement of retractor member 431. For example, a distal end of spring member 433 may be coupled to housing 424 in any suitable manner as may serve a particular implementation.

As shown, retractor member 431 may include an annular recess 435. In some examples, annular recess 435 may be configured to be selectively engaged by one or more components of slider assembly 420 to retain retractor member 431 relative to slider assembly 420. For example, annular recess 435 may be configured to be selectively engaged by a proximal portion of rocker lever 428.

Backstop 434 may be configured to limit the movement of retractor member 431. For example, a proximal end of backstop 434 may be configured to contact handle portion 411 when retractor member 431 is in the proximal position to prevent further movement of retractor member 431 in a proximal direction. Backstop 434 may be configured to allow or prevent any amount of movement of retractor member 431 as may be suitable for a particular implementation. Additionally or alternatively, backstop 434 may be configured to absorb energy created by the contact between backstop 434 and handle portion 411.

In some examples, retractor assembly 430 may be configured to be reset to a distal position in response to actuation by a user of slider assembly 420. For example, a user may return slider member 422 to the first position thereby allowing rocker lever 428 to reengage retractor member 431 to again retain retractor member 431 relative to slider assembly 420. As a result, the user may use insertion tool 400 again (e.g., to insert another lead into another bodily orifice).

Retractor member 431, spring member 433, and/or backstop 434 may be made out of any suitable material as may serve a particular implementation. For example, retractor member 431, spring member 433, and/or backstop 434 may be made out of stainless steel, titanium, a hard plastic, any other suitable material, and/or combinations thereof.

Insertion tool 400 is provided for illustrative purposes and is not limiting. Insertion tool 400 may include additional or alternative elements and/or may exclude certain illustrated elements according to principles described herein.

Figure 9:
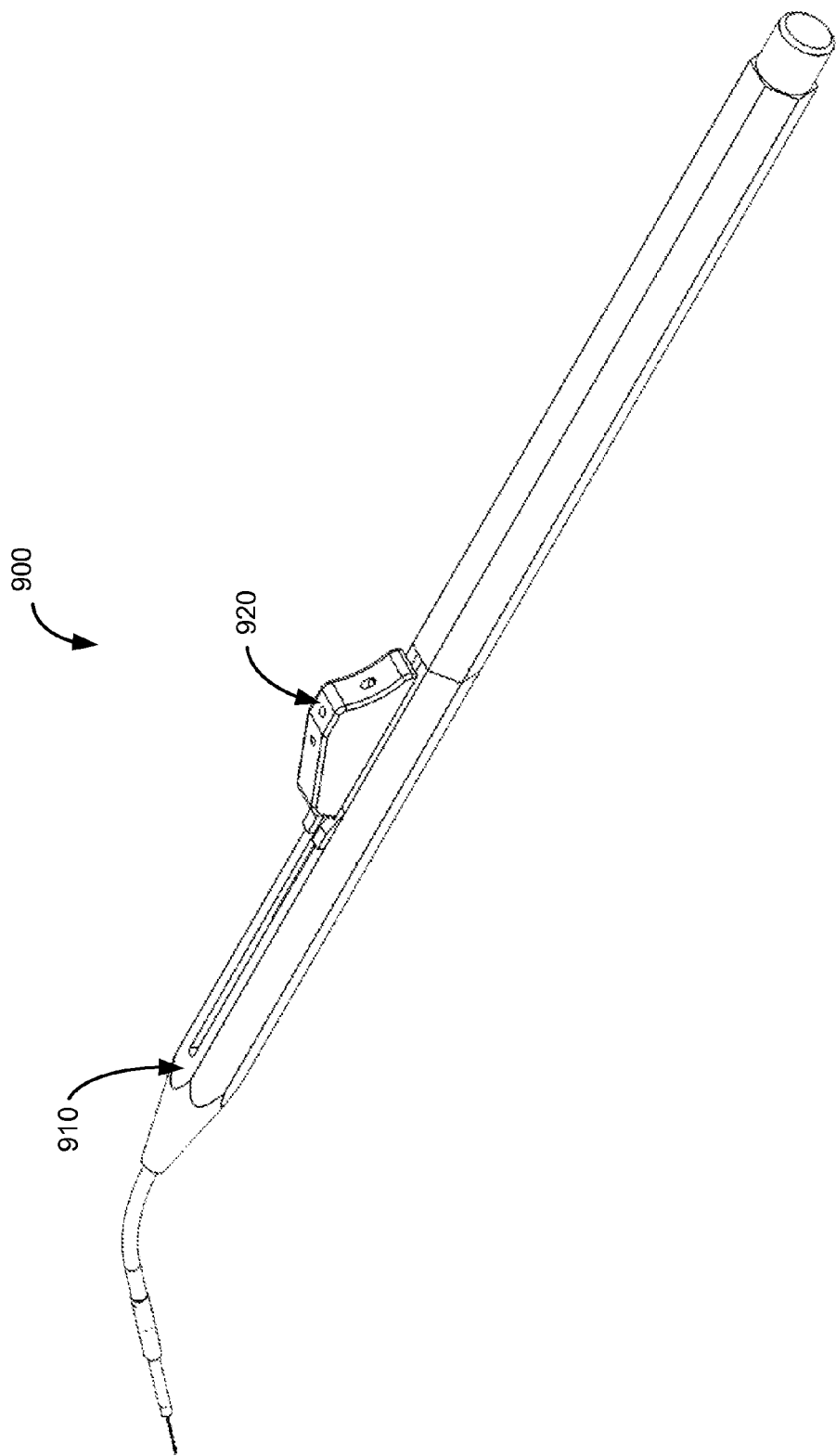
FIG. 9 is a perspective view of another exemplary insertion tool according to principles described herein.

FIG. 9 is a perspective view of another exemplary insertion tool 900 configured to facilitate insertion of an electrode array portion of a lead into a bodily orifice according to principles described herein. Insertion tool 900 may be similar in some respects to insertion 400 described herein. Accordingly, some aspects of insertion tool 900 may not be described in detail with respect to this configuration as they are already described with respect to insertion tool 400. Like elements may be designated with like reference numerals.

Figure 10A:
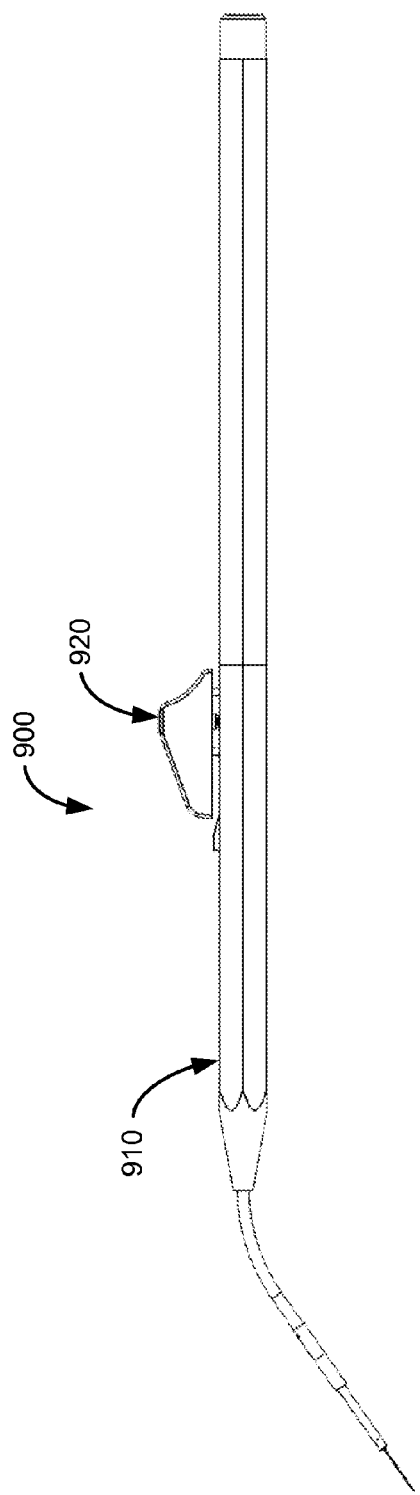
FIG. 10A is a side view of the exemplary insertion tool of FIG. 9 according to principles described herein.
Figure 10B:
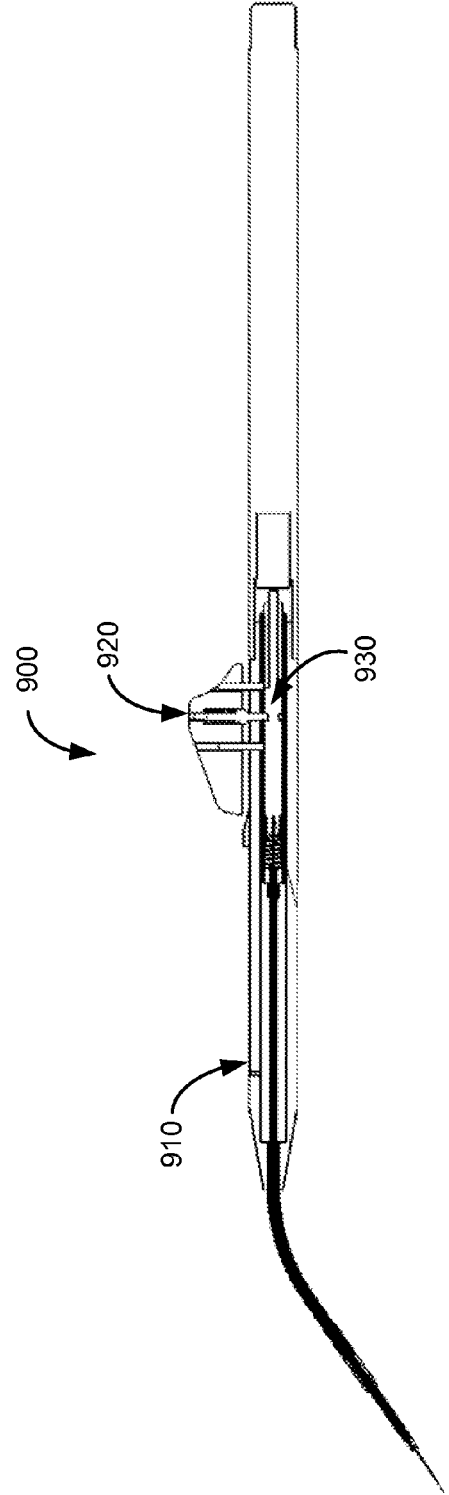
FIG. 10B is a cross-sectional side view of the exemplary insertion tool of FIG. 9 according to principles described herein.

Insertion tool 900 is shown in greater detail in FIG. 10A, which illustrates a side-view of insertion tool 900, and FIG. 10B, which illustrates a cross-sectional side view of insertion tool 900. As shown, insertion tool 900 may include a handle assembly 910, a slider assembly 920 disposed at least partially within and slidable relative to handle assembly 910, and a retractor assembly 930 disposed at least partially within handle assembly 910 and/or slider assembly 920. Each of the components of insertion tool 900 and the interaction between the components of insertion tool 900 will now be described in more detail.

As mentioned above, insertion tool 900 may include handle assembly 910. Handle assembly 910 may be configured to facilitate handling of insertion tool 900 by a user (e.g., a surgeon) and/or contain one or more other components of insertion tool 900. Handle assembly 910 is shown in more detail in FIG. 11A, which illustrates a side view of handle assembly 910, and FIG. 11B, which illustrates a cross-sectional side view of handle assembly 910. Handle assembly 910 may be similar in many respects to handle assembly 410, described in more detail above.

For example, as shown, handle assembly 910 may include a handle portion 911, a guide tube 912 coupled to a distal end of the handle portion 911, and a holder member 913 coupled to a distal end of guide tube 912. Handle portion 911 may be configured to be gripped and/or handled by a user (e.g., a surgeon) of insertion tool 900 and may house one or more other components of insertion tool 900. In addition, handle portion may include a handle slot 914 extending along a length thereof and configured to allow one or more components of insertion tool 900 (e.g., slider assembly 920) to extend through handle slot 914 and/or move relative to handle portion 911 within handle slot 914. Guide tube 912 may be coupled to a distal end of handle portion 911 and may be configured to at least partially contain one or more other components of insertion tool 900. Additionally or alternatively, holder member 913 may be coupled to a distal end of guide tube 912 and configured to removably couple to a lead, as described in more detail herein.

In some examples, handle assembly 910 may include one or more plunger ramps 915 coupled to handle portion 911. Plunger ramps 915 may be configured to engage and actuate one or more components of slider assembly 920. For example, plunger ramps 915 may be configured to engage and actuate a plunger member of slider assembly 920, as will be explained in more detail below. In certain embodiments, handle assembly 910 may include a first plunger ramp 915 on a first side of handle slot 914 and a second plunger ramp 915 on a second side of handle slot 914. Alternatively, handle assembly 910 may include more or fewer plunger ramps 915 as may be suitable for a particular implementation.

Returning to FIGS. 9, 10A, and 10B, insertion tool 900 may include slider assembly 920 disposed at least partially within and slidable relative to handle assembly 910. Slider assembly 920 may be configured to be actuated by a user to operate insertion tool 900. For example, slider assembly 920 may be configured to be actuated by a user to advance an electrode array portion of a lead in a distal direction relative to handle assembly 910 and/or at least partially retract a stiffening member from the electrode array portion, as explained in more detail herein.

Slider assembly 920 is shown in greater detail in FIG. 12A, which illustrates a side view of slider assembly 920, and FIG. 12B, which illustrates a cross-sectional side view of slider assembly 920. Slider assembly 920 may be similar in some respects to slider assembly 420, described in more detail herein. For example, slider assembly 920 may include a slider member 922, a slider housing 924, a tubular member 926 coupled to a distal end of slider housing 924, and a plunger member 928 coupled to slider member 922.

Slider member 922 may be configured to be actuated (e.g., advanced in a distal direction relative to handle assembly 910) by a user to perform one or more of the functions of insertion tool 900 described herein. For example, slider member 922 may be configured to slide relative to handle assembly 910 between a first position and a second position. In some examples, slider assembly 920 may be configured to advance an electrode array portion of a lead in a distal direction relative to handle assembly 910 as slider member 922 moves from a first position towards a second position. For example, tubular member 926 may be configured to engage and advance a lead as slider member 922 moves from the first position towards the second position. Additionally or alternatively, slider assembly 920 may be configured to selectively retain one or more components of retractor assembly 930 relative to slider assembly 920 and release the one or more components of retractor assembly 930 in response to actuation by a user of slider member 922. For example, plunger member 928 may be configured to selectively retain retractor assembly 930 and then release retractor assembly 930 in response to actuation by the user of slider member 922.

In some examples, plunger member 928 may be disposed at least partially within slider member 922 and may be movable between an extended position and a retracted position. For example, plunger member 928 may be configured to extend at least partially into slider housing 924 (e.g., to engage retractor assembly 930) when in the extended position and to retract from slider housing 924 (e.g., to release retractor assembly 930) when in the retracted position. Additionally or alternatively, plunger member 928 may be spring-loaded with a spring member disposed between slider member 922 and plunger member 928. As a result, plunger member 928 may be biased towards the extended position.

Plunger member 928 may be configured to be engaged and actuated (e.g., moved from an extended position to a retracted position) by plunger ramps 915. For example, plunger ramps 915 may be configured to engage and actuate plunger member 928 when slider member 922 is in the second position. As a result, plunger member 928 may release one or more components of retractor assembly 930, as explained in more detail herein.

Returning to FIG. 10B, as shown, insertion tool 900 may include a retractor assembly 930 disposed at least partially within and slidable relative to handle assembly 910 and/or slider assembly 920. Retractor assembly 930 is shown in greater detail in FIG. 13A, which illustrates a side view of retractor assembly 930, and FIG. 13B, which illustrates a cross-sectional side view of retractor assembly 930. Retractor assembly 930 may be similar in some respects to retractor assembly 430, described in more detail above. For example, as shown, retractor assembly 930 may include a retractor member 931, a stiffening member 932 coupled to and extending from a distal end of retractor member 931, a spring member 933 coupled to retractor member 931, and a backstop 934 coupled to a proximal end of retractor member 931.

In some examples, a distal end of stiffening member 932 may be configured to be inserted into an electrode array portion of a lead to provide sufficient stability to insert the electrode array portion into a cochlea. Retractor assembly 930 may be configured to thereafter at least partially retract stiffening member 932 from the electrode array portion. For example, retractor member 931 may be configured to move from a distal position to a proximal position (e.g., by way of force exerted by spring member 933) in response to actuation by a user of slider member 922 to at least partially retract stiffening member 932 from an electrode array portion of a lead. Additionally or alternatively, retractor member 931 may include an annular recess 935 configured to be selectively engaged by plunger member 928.

Insertion tool 900 is provided for illustrative purposes only and is not limiting. Insertion tool 900 may include additional or alternative elements and/or may exclude certain illustrated elements according to principles described herein.

Figure 14:
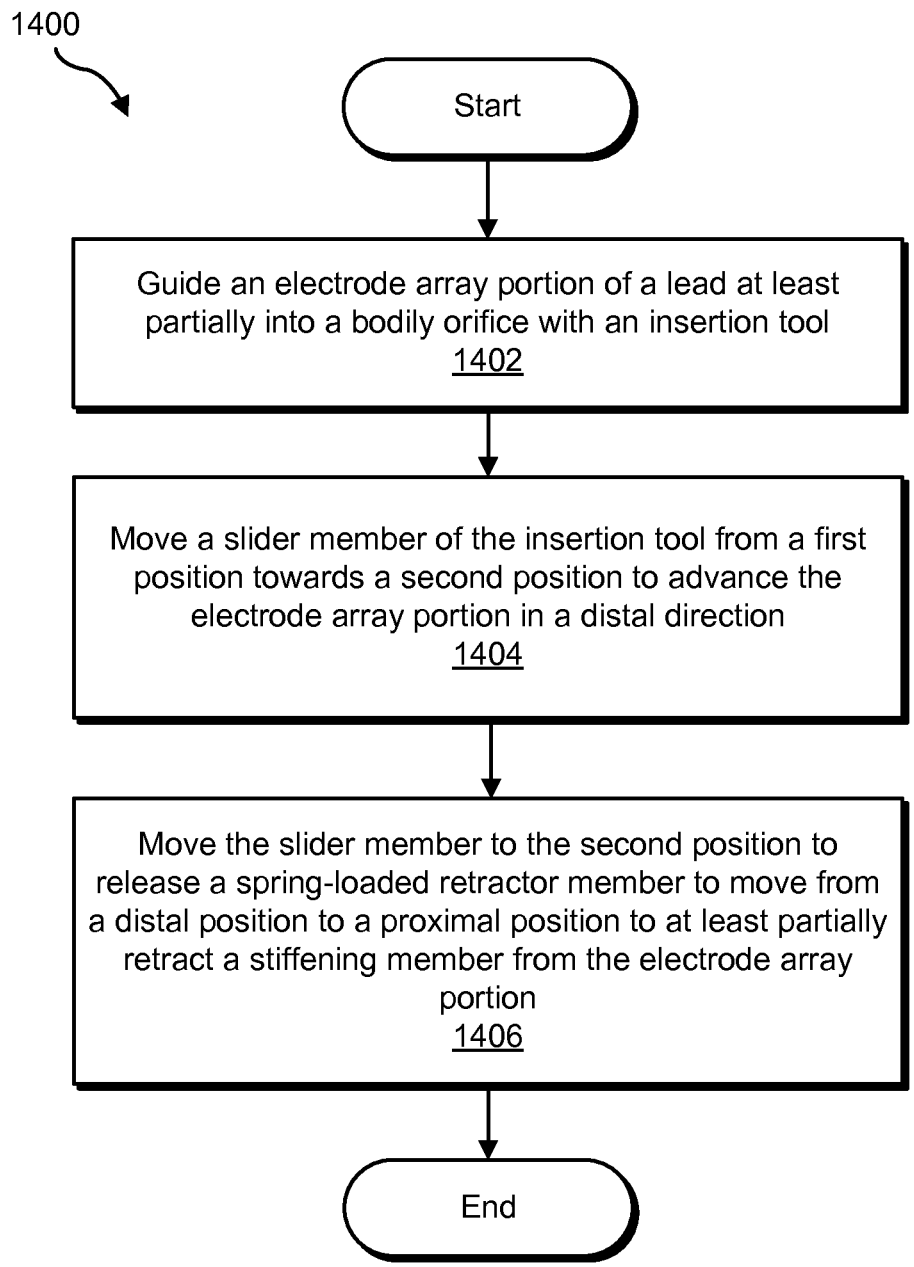
FIG. 14 illustrates an exemplary method of inserting an electrode array portion of a lead into a bodily orifice according to principles described herein.

FIG. 14 illustrates an exemplary method 1400 of inserting an electrode array portion of a lead into a bodily orifice. While FIG. 14 illustrates exemplary steps according to one embodiment, other embodiments may omit, add to, reorder, and/or modify any of the steps shown in FIG. 14.

Figure 15A:
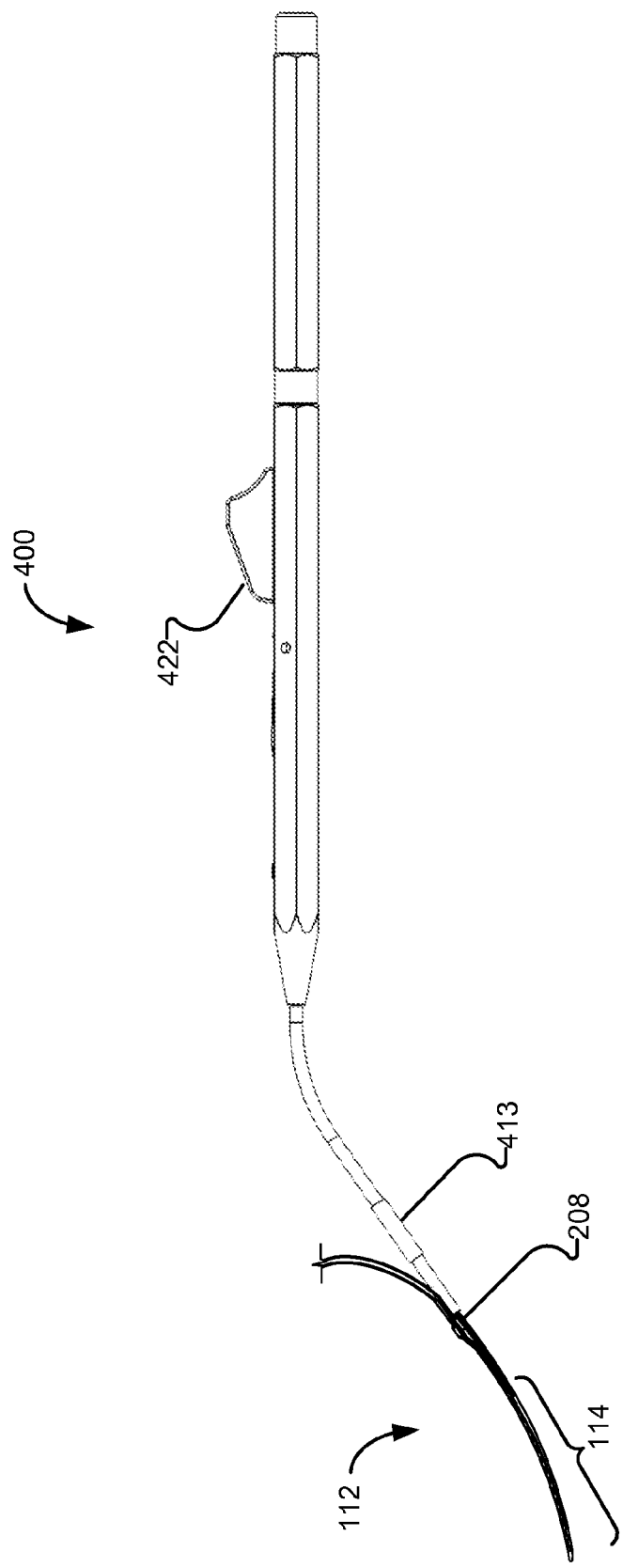
FIG. 15A shows an exemplary lead coupled to an exemplary insertion tool according to principles described herein.

In step 1402, an electrode array portion of a lead may be guided at least partially into a bodily orifice with an insertion tool. For example, FIG. 15A illustrates lead 112 coupled to insertion tool 400. Insertion tool 400 is shown for illustrative purposes only. In additional or alternative examples, any other insertion tool described herein (e.g., insertion tool 900) may be utilized in accordance with method 1400.

In some examples, molded feature 208 of lead 112 may be removably coupled to holder member 413 and stiffening member 432 (FIGS. 8A and 8B) may be at least partially inserted into lead 112 (e.g., into lumen 150, FIG. 2). As shown in FIG. 15A, to facilitate coupling of stiffening member 300 to insertion tool 400, slider member 422 may be in a first position. While slider member 422 is in the first position, retractor member 431 (FIGS. 8A and 8B) may be retained in a distal position, as explained in more detail herein.

Figure 15B:
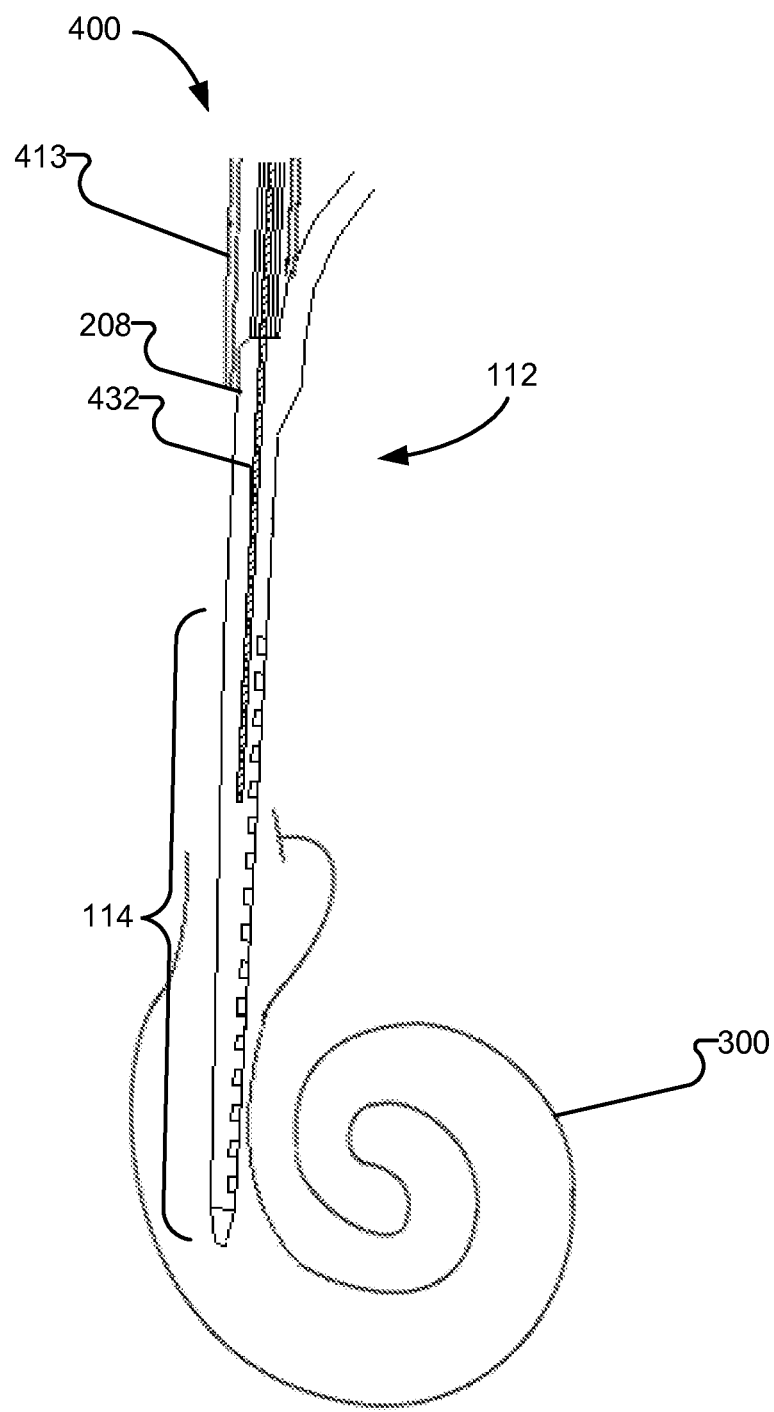
FIG. 15B shows an exemplary electrode array portion of the exemplary lead of FIG. 15A being inserted into an exemplary cochlea according to principles described herein.

Insertion tool 400 may be used to guide electrode array portion 114 at least partially into a bodily orifice. For example, FIG. 15B shows electrode array portion 114 of lead 112 being guided into cochlea 300 with insertion tool 400. As shown, stiffening member 432 may be inserted at least partially into lead 112. In some examples, stiffening member 432 may provide stability and/or stiffness to lead 112 as electrode array portion 114 is guided into cochlea 300.

Figure 15D:
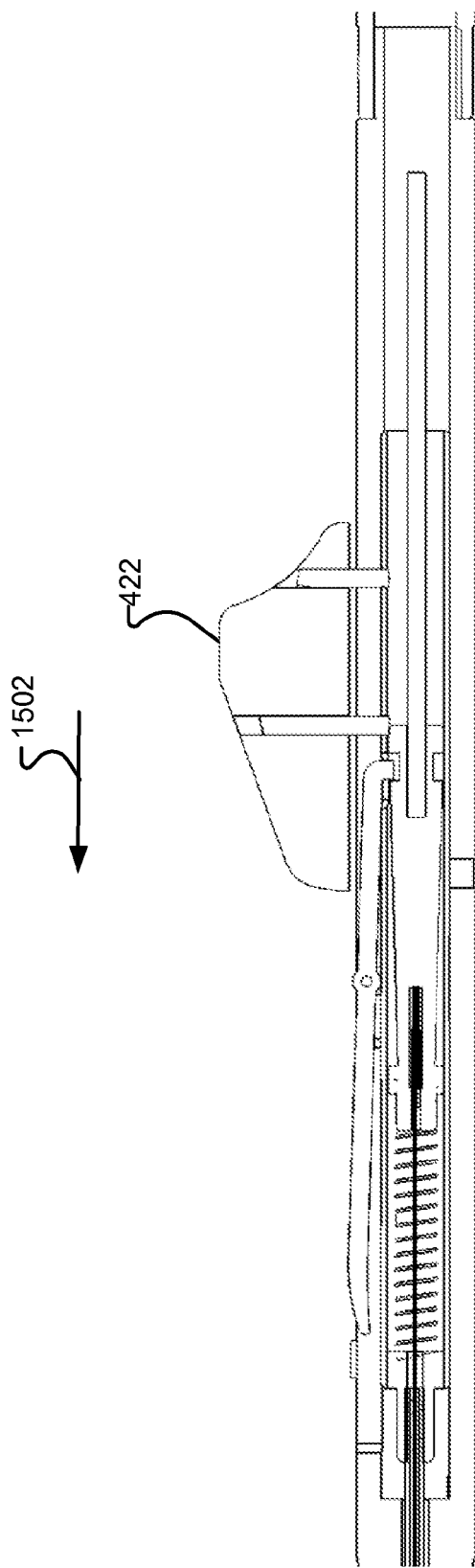
FIG. 15D shows a cross-sectional side view of the exemplary slider assembly of FIG. 15C being moved from a first position towards a second position according to principles described herein.
Figure 15E:
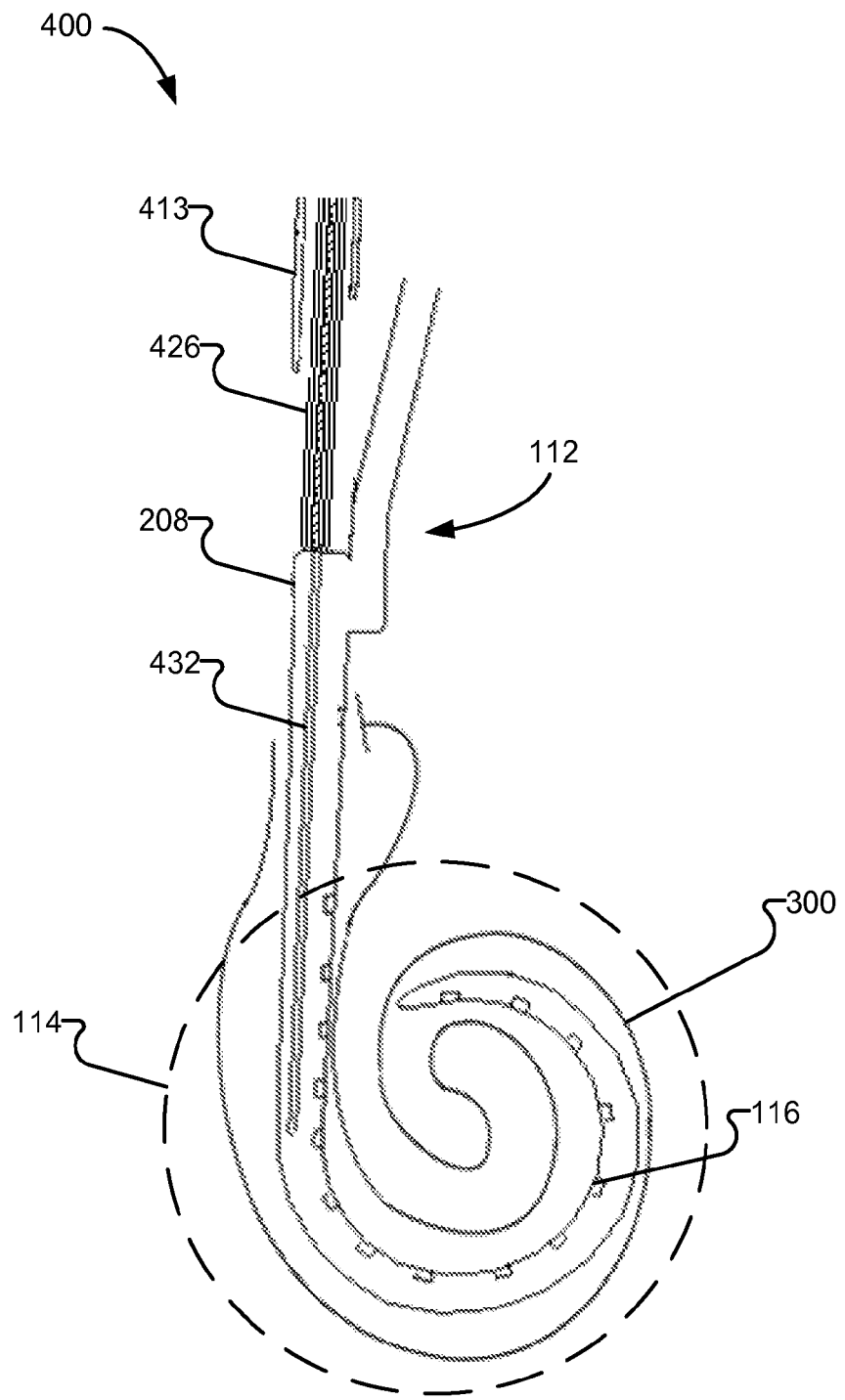
FIG. 15E shows the exemplary electrode array portion being advanced into the exemplary cochlea according to principles described herein.

Returning to FIG. 14, in step 1404, a slider member of the insertion tool may be moved from a first position towards a second position to advance the electrode array portion in a distal direction relative to a handle assembly of the insertion tool. For example, slider member 422 of insertion tool 400 may be moved from a first position (as shown in FIG. 15C) towards a second position. FIG. 15D show slider member 422 being moved in a direction indicated by arrow 1502 towards a second position. Movement of slider member 422 in a distal direction towards the second position may cause the other components of slider assembly 920 and may cause retractor assembly 430 to move in a distal direction relative to handle assembly 410. As a result, tubular member 426 of slider assembly 420 and/or stiffening member 432 of retractor assembly 430 may engage and advance lead 112 in a distal direction relative to holder member 413. For example, FIG. 15E shows lead 112 being advanced relative to holder member 413 and further into cochlea 300 in response to movement of tubular member 426 and stiffening member 432. Additionally or alternatively, electrode array portion 114 may conform to the geometry of cochlea 300 thereby positioning electrodes 116 of electrode array portion 114 such that they face the auditory nerve tissue of cochlea 300.

Returning to FIG. 14, in step 1406, the slider member may be moved to the second position to release a spring-loaded retractor member of the insertion tool to move from a distal position to a proximal position to at least partially retract a stiffening member from the electrode array portion. For example, FIG. 15F shows slider member 422 moved to the second position. As shown, moving slider member 422 to the second position may cause a distal portion of rocker lever 428 to engage striker plate 415, thereby causing rocker lever 428 to pivot. As a result, a proximal portion of rocker lever 428 may disengage and release retractor member 431 to move from a distal position (e.g., as shown in FIG. 15D) to the proximal position shown in FIG. 15F.

Figure 15G:
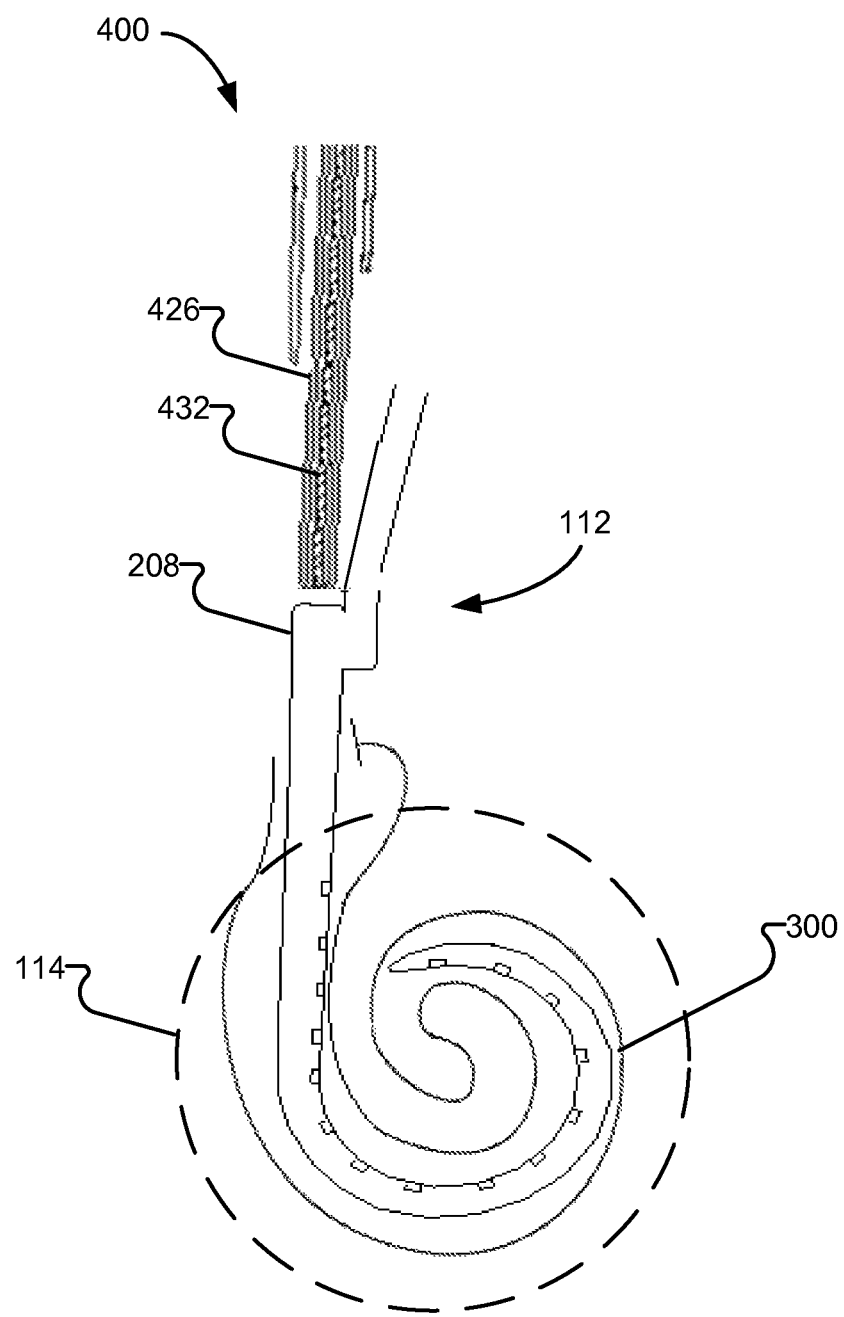
FIG. 15G shows an exemplary stiffening member being retracted from the electrode array portion according to principles described herein.

As shown in FIG. 15G, movement of retractor member 431 from the distal position to the proximal position may at least partially retract stiffening member 432 from electrode array portion 114 and/or lead 112. As a result, lead 112 may be released from insertion tool 400 thereby allowing a user to retract insertion tool 400 away from cochlea 300, leaving lead 112 in place with electrode array portion 114 within cochlea 300.

Figure 15H:
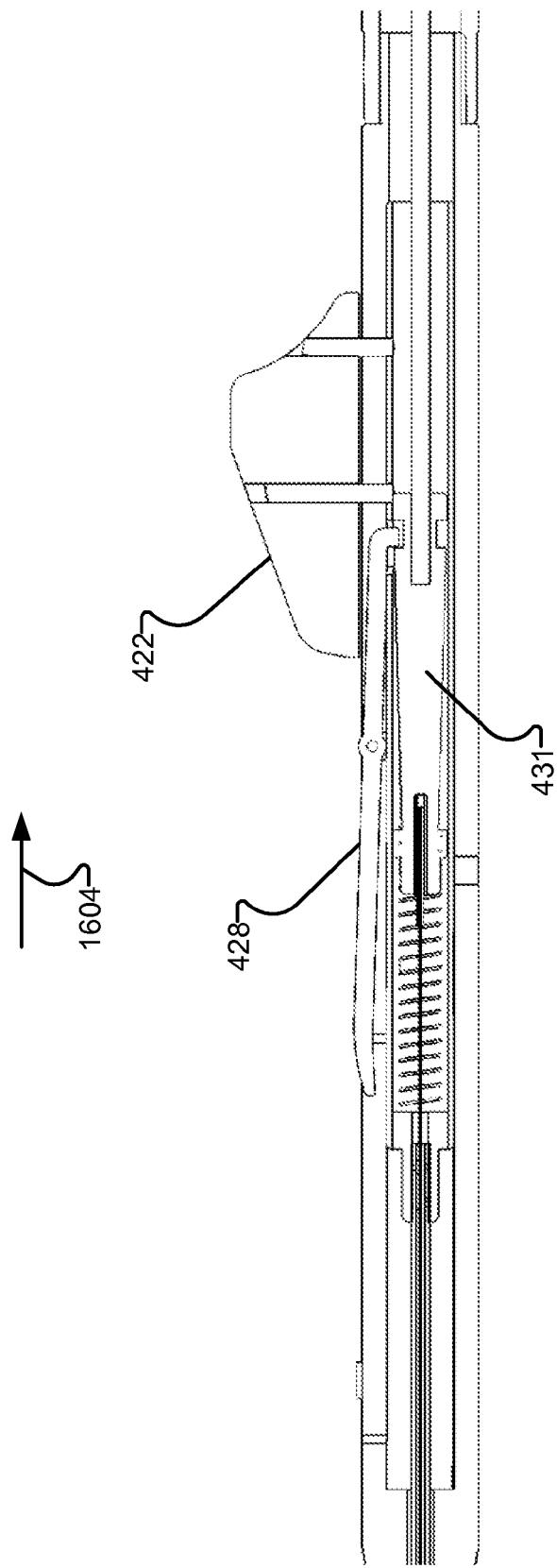
FIG. 15H shows a cross-sectional side view of the slider assembly returned to the first position according to principles described herein.

Additionally or alternatively, the user may reset retractor member 431. For example, as shown in FIG. 15H, a user may return slider member 422 from the second position to the first position by moving slider member 422 in the direction indicated by arrow 1504. Returning slider member 422 to the first position may allow rocker lever 428 to reengage retractor member 431 to again retain retractor member 431 relative to slider assembly 420, thereby allowing insertion tool 400 to be re-used to insert another electrode array portion of another lead into another bodily orifice.

The insertion tools described herein may be configured to facilitate single-handed insertion of a lead into a bodily orifice. For example, a user may grasp handle portion 411 of insertion tool 400 with a single hand and guide electrode array portion 114 into the cochlear duct. Once electrode array portion 114 has been suitably positioned, the user may retract stiffening member 432 from electrode array portion 114 utilizing insertion tool 400 by actuating slider member 422. This may be performed without substantially repositioning insertion tool 400 within the user's hand. In this manner, insertion tool 400 may provide a stable platform for the insertion of electrode array portion 114 and minimize trauma to the cochlea that may occur during the insertion procedure.

In some examples, insertion tools described herein and/or any components thereof may be disposable. For example, insertion tool 400 and/or insertion tool 900 may be used during a single electrode array portion insertion procedure (or during two electrode array portion insertion procedures for a bilateral cochlear implant patient) and then disposed of. In this manner, insertion tool 400 and/or insertion tool 900 does not need to be sterilized after use. Alternatively, insertion tool 400 and/or insertion tool 900 may be sterilized after use so that it may be used in one or more subsequent insertion procedures.

Insertion tools 400 and 900 are provided for exemplary purposes only and are not limiting. Additional insertion tools according to principles described herein may include additional or alternative elements and/or may exclude certain illustrated elements according to principles described herein.

The preceding description has been presented only to illustrate and describe embodiments of the invention. It is not intended to be exhaustive or to limit the invention to any precise form disclosed. Many modifications and variations are possible in light of the above teaching.

What is claimed is:

1. An insertion tool configured to facilitate insertion of an electrode array portion of a lead into a bodily orifice, the insertion tool comprising:
   a handle assembly configured to facilitate handling of the insertion tool;
   a retractor assembly disposed at least partially within the handle assembly and comprising a stiffening member configured to be inserted into the electrode array portion and a spring-loaded retractor member coupled to the stiffening member, wherein the spring-loaded retractor member is configured to move from a distal position to a proximal position relative to the handle assembly to at least partially retract the stiffening member from the electrode array portion; and
   a slider assembly disposed at least partially within the handle assembly and configured to selectively retain the spring-loaded retractor member relative to the slider assembly, wherein the slider assembly is further configured to release the spring-loaded retractor member to move from the distal position to the proximal position relative to the handle assembly in response to an advancement by a user of the slider assembly in a distal direction relative to the handle assembly.

2. The insertion tool of claim 1, wherein the slider assembly comprises a slider member slidable relative to the handle assembly between a first position and a second position in response to actuation of the slider member by the user.

3. The insertion tool of claim 2, wherein the slider assembly and the stiffening member are configured to advance the electrode array portion relative to the handle assembly as the user moves the slider member in the distal direction from the first position to the second position.

4. The insertion tool of claim 3, wherein the slider assembly comprises a rocker lever configured to selectively retain the spring-loaded retractor member relative to the slider assembly.

5. The insertion tool of claim 4, wherein the handle assembly comprises a striker plate configured to engage and pivot the rocker lever when the slider member is in the second position to release the spring-loaded retractor member from the distal position to the proximal position to at least partially retract the stiffening member from the electrode array portion.

6. The insertion tool of claim 3, wherein the slider assembly comprises a tubular member configured to engage and advance the electrode array portion relative to the handle assembly as the slider member moves in the distal direction from the first position towards the second position.

7. The insertion tool of claim 6, wherein the stiffening member is configured to advance relative to the handle assembly with the electrode array portion as the slider member moves in the distal direction from the first position towards the second position, and wherein the stiffening member is further configured to provide stability to the electrode array portion as the electrode array portion is inserted into the bodily orifice.

8. The insertion tool of claim 3, wherein the slider assembly comprises a spring-loaded plunger configured to selectively retain the spring-loaded retractor member relative to the slider assembly.

9. The insertion tool of claim 8, wherein the handle assembly comprises a plunger ramp configured to engage the spring-loaded plunger when the slider assembly is in the second position to release the spring-loaded retractor member from the distal position to the proximal position to at least partially retract the stiffening member from the electrode array portion.

10. The insertion tool of claim 1, wherein the slider assembly comprises a slider housing configured to at least partially house the spring-loaded retractor member.

11. The insertion tool of claim 1, wherein the handle assembly comprises a handle portion configured to at least partially house the retractor assembly and the slider assembly, a guide tube coupled to a distal end of the handle portion, and a holder member coupled to a distal end of the guide tube and configured to removably couple to the lead.

12. The insertion tool of claim 11, wherein a distal portion of the holder member comprises a slot configured to hold a portion of the lead.

13. The insertion tool of claim 12, wherein the holder member is configured to be rotatable relative to the guide tube to facilitate selective insertion of the electrode array portion in a right cochlea or a left cochlea.

14. The insertion tool of claim 1, wherein the stiffening member is configured to insert into a lumen that extends along a length of the electrode array portion.

* * * * *